United States Patent [19]

Cano et al.

[11] 4,242,501
[45] Dec. 30, 1980

[54] PURIFICATION OF PNEUMOCOCCAL CAPSULAR POLYSACCHARIDES

[75] Inventors: Francis J. Cano, Spring Valley; Joseph S. C. Kuo, Orangeburg, both of N.Y.; Merle V. Querry, River Vale, N.J.

[73] Assignee: American Cyanamid Company, Stamford, Conn.

[21] Appl. No.: 64,663

[22] Filed: Aug. 8, 1979

[51] Int. Cl.³ .................... C07H 3/00; C08B 37/00
[52] U.S. Cl. .................................. 536/1; 424/92; 424/180; 536/18
[58] Field of Search ............... 424/92, 180; 536/1

[56] References Cited

FOREIGN PATENT DOCUMENTS 2404 6/1979 opean Pat. Off. .................... 424/92

OTHER PUBLICATIONS

Borgono, J., et al., Proc. Soc. Exp. Biol. Med., vol. 157, 148–154 (1978).
Smit, P., et al., Biol. Abstracts, vol. 65, 39335 (1978).
Hilleman, M., et al., Biol. Abstracts, vol. 67, 28387 (1979).
Cowan, M., et al., Chem. Abstracts, vol. 90, 20714x (1979).
Glaudemans, C., et al., Carbohyd. Res., vol. 4, 181–184, (1967).
Williams, C., et al., Methods in Immunology and Immunochemistry, vol. I, 52–60, Academic Press, New York, 1967.

Primary Examiner—Johnnie R. Brown
Assistant Examiner—Blondel Hazel
Attorney, Agent, or Firm—Thomas M. Saunders

[57] ABSTRACT

A multivalent pneumococcal vaccine of the group consisting of immunogenic amounts of purified pneumococcal capsular polysaccharide (substantially absent "C" polysaccharide) of pneumococcal types (Danish designation) 1, 2, 3, 4, 6A, 6B, 7F, 8, 9N, 12F, 14, 18C, 19F, 20, 23F, and 25 and combinations thereof and methods of purifying pneumococcal capsular polysaccharide types 1, 2, 3, 4, 6A, 6B, 7F, 8, 9N, 12F, 14, 18C, 19F, 23F and 25.

85 Claims, No Drawings

PURIFICATION OF PNEUMOCOCCAL CAPSULAR POLYSACCHARIDES

BACKGROUND OF THE INVENTION

This invention is concerned with a multivalent pneumococcal vaccine consisting of purified pneumococcal capsular polysaccharide with the "C" polysaccharide substantially absent. This invention is also concerned with the specific purification of each of 16 pneumococcal types which by Danish designation are types 1, 2, 3, 4, 6A, 6B, 7F, 8, 9N, 12F, 14, 18C, 19F, 20, 23F and 25, to yield the purified immunogenic polysaccharides of the invention.

Pneumococcal cultures of each type useful in this invention are stored and available worldwide from a great number of culture libraries. The American Type Culture Collection (ATCC), 12301 Parklawn Drive, Rockville, Maryland, U.S.A. 20852, lists all the pneumococcal types of this invention as being freely available.

The 1978 ATCC catalogue designates these types as follows: (See Table I)

TABLE I

| Danish Type Nomenclature | U.S. Nomenclature | Catalogue Number |
| --- | --- | --- |
| 1 | 1 | 6301 |
| 2 | 2 | 6302 |
| 3 | 3 | 6303 |
| 4 | 4 | 6304 |
| 6A | 6 | 6306 |
| 6B | 26 | 6326 |
| 7F | 51 | 10351 |
| 8 | 8 | 6308 |
| 9N | 9 | 6309 |
| 12F | 12 | 6312 |
| 14 | 14 | 6314 |
| 18C | 56 | 10356 |
| 19F | 19 | 6319 |
| 20 | 20 | 6320 |
| 23F | 23 | 6323 |
| 25 | 25 | 6325 |

The critical step in the preparation of a vaccine is purification of the immunogenic material such that extraneous material is removed without loss of those properties of the retained material that will cause the appropriate antibody production. Such properties of polysaccharide appear to reside in the retention of what may be termed the "native state configuration" of the polysaccharide.

Among those materials to be separated from the polysaccharide are proteins, nucleic acids and "C" polysaccharide. "C" polysaccharide is found in high concentration in Danish designation pneumococcal types 4, 7F, and 14.

"C" polysaccharide is a choline containing teichoic acid on the cell wall of pneumococcus and is species specific. It is further described in Tomasz, A., Science 157 694 (1967) and Brundish, D. E., and Baddeley, J., Biochem. J. 110 573 (1968) and Nosser, J. L., Tomasz, A., J. Biol. Chem. 245 #2, 287, (1970).

Nucleic acids (which absorb light at 260 MMU) are difficult to reduce to a satisfactory level in preparations of pneumococcal polysaccharides. This problem is in contradistinction to the situation presented by meningiococcal polysaccharide which is more easily purified while retaining immunogenicity. Meningiococcal polysaccharides may be purified by relatively harsh methods as shown in U.S. Pat. No. 3,636,192 to Gotschlich.

There are 85 specific types of pneumococcus. These types are designated by both American and Danish numbering systems. Type designations cited herein are to the Danish numbering. Each type appears to require a particular method for eliminating contaminants but no single method is applicable to all types of pneumococcal polysaccharide. Further the specific proper method appears to be unpredictable. As exemplary of the different procedures used to purify various pneumococcal polysaccharides, some require a large volume of ethanol for precipitation, such as Type 7F which can be partially separated from nucleic acids by fractional precipitation as the nucleic acids are precipitated in the 30–50%* alcohol ranges using 3A alcohol.

[* % alcohol ranges refer to the volume of alcohol used related to the solutions original volume. 3A alcohol is 5% absolute methanol and 95% absolute ethanol. Absolute ethanol would behave in an essentially identical manner and is considered fully equivalent. Throughout this specification the term "alcohol" will designate 3A alcohol unless otherwise specified.]

With other types, such as Type 3, polysaccharides are precipitated in the 30–50% range thus alcohol is not effective as a separatory precipitant. In contrast, types 1, 8 and 12 can be separated from nucleic acids by carefully controlled amounts of protamine sulfate. With these types at an optimal concentration of protamine sulfate (0.02–0.20%), nucleic acids are precipitated and can be pelleted by high speed centrifugation. However, any excess protamine sulfate in the system beyond the minimum amount required to precipitate the constituent nucleic acid will additionally precipitate the polysaccharide. An example of another type of purification of pneumococcal polysaccharide is presented by the purification often used for Type 3 pneumococcus, which is difficult to separate from nucleic acid. If calcium acetate is substituted for sodium acetate as the electrolyte in a solution of Type 3 pneumococcal polysaccharide, the polysaccharide can be precipitated with a minimal amount of alcohol (10–12%). However, this method sometimes allows substantial amounts of nucleic acid to remain soluble in the supernatant phase. The behavior of various pneumococcal polysaccharide types in a reaction of the polysaccharide-nucleic acid mixtures with ammonium sulfate is also variable. Some polysaccharides are precipitated by ammonium sulfate salt at 50–60% saturation whereas others are not. Type 1 polysaccharide is not precipitated with ammonium sulfate whereas Type 3 and Type 4 may be separated to some degree from nucleic acids by 50% saturation with ammonium sulate. From the foregoing exposition and from the following references (Guy, R. C. W., How, J., Stacey, M., Heidelberger, M., J. Biol Chem. 242 21 (1967); Brown, R., J. Immunol. 37 455 (1939); Glaudemans, C. P. J., Treffers, H. P., Carbohydrate Res. 4, (1967); Kabat, E. A., Exp. Immunochemistry, Charles C. Thomas, publisher, pp. 838–842 (1967)) it can be seen that there is no one satisfactory method for the removal of contaminants from pneumococcal polysaccharide applicable to all types in view of the fact that there are 85 or more types of pneumococcus and the production of a practical vaccine usually requires a multivalent vaccine comprising polysaccharide fractions from many species of pneumococcus, each retaining a relatively native state configuration.

Another contaminant of pneumococcal polysaccharide is protein. Although alcohol precipitation is effective in reducing the level of protein contamination it is unable to reduce the contamination to a level satisfactory for a parenteral product. One method commonly employed to reduce the level of protein is to subject a mixture of pneumococcal polysaccharides and protein to organic solvents. For example, the "Sevag" procedure [Sevag, M. G. Biochem. Z., 272 419 (1934)] involves extraction of chloroform and butanol mixtures shaken vigorously for 4–6 hours and then subjected to low speed centrifugation. Denatured protein which collects at the interface can then be separated from the aqueous phase with the polysaccharides. However, this procedure is unsatisfactory as the extraction often adversely affects the pneumococcal polysaccharides causing their breakdown, depolymerization or loss of native state configuration. The result is polysaccharide that is not effective as an immunogen. Other procedure may be employed to reduce protein contamination such as ammonium sulfate precipitation and molecular sieving but such procedures are specific to each group of proteins and peptides among the many different sizes and types of proteins in the solution. Here again the variability of the polysaccharides, depending the on strain, determines the effectiveness the particular protein separatory step employed. Further, one many conclude that no one procedure is effective in purifying all pneumococcal capsular polysaccharides, and prediction of the behavior of a particular pneumococcal capsular polysaccharide appears impossible.

However, a number of methods of purifying pneumococcal capsular polysaccharide, with high purity and retention of immunogenic properties have now been discovered. These purifications have been specifically directed to the purification of 16 types of pneumococcus. These types are 1, 2, 3, 4, 6A, 6B, 7F, 8, 9N, 12F, 14, 18, 19F, 20, 23F, and 25 (Danish designation).

SUMMARY OF THE INVENTION

The subject of this invention is a multivalent vaccine of a combination of effective immunogenic amounts of the pneumococcal capsular polysaccharide from the group, by Danish designation, types 1, 2, 3, 4, 6A, 6B, 7F, 8, 9N, 12F, 14, 18C, 19F, 20, 23F and 25 and substantially absent "C" polysaccharide, a major contaminant of types 4, 7F, and 14. As defined in this specification, substantially absent "C" polysaccharide refers to less than 0. % "C" polysacharide. Central to the preparation of this multivalent vaccine is the method of preparing the purified capsular polysaccharide of each of the 16 types used in this vaccine. After the pneumococcus bacteria has been grown by any suitable method of fermentation to stationary growth phase the fermentation is stopped by the addition of an effective amount of sodium desoxycholate to lyse all bacterial cells and release cell-associated polysaccharide into the medium. Cellular debris is removed from the medium to be followed by one or two alcohol precipitations. This procedure removes a great deal of the contaminating protein and other contaminants from the pneumococcal polysaccharides.

Carefully controlled alcohol precipitation is a major step in the instant process in the purification of all the polysaccharides, with each polysaccharide being precipitated at least 5 times by alcohol. This avoids the more harsh chloroform-butanol extraction.

Two types of alcohol precipitation are used.

In the first, sufficient alcohol is added to the sample to precipitate the polysaccharides. The pellet is then separated from the supernatant by centrifugation and redissolved in distilled water.

The second type is a fractional alcohol precipitation. The maximum amount of alcohol is added which does not precipitate the polysaccharides. The pellet of contaminants is then removed by centrifugation and sufficient alcohol is then added to the supernatant to precipitate the polysaccharides. The polysaccharide pellet is then harvested by centrifugation and the polysaccharides are redissolved in distilled water.

At the end of both typs of precipitation, any particular matter undissolved in the water is not polysaccharide and is removed by centrifugation.

The hexadecyltrimethylammonium bromide (cetavlon) treatment of pneumococci, follows several alcohol precipitations to be most effective, being an improvement over if used at earlier stages in the purification procedure.

Cetavlon, with most of the pneumococcal types of the present invention, is a critical separatory step. In these types, this step under carefully controlled conditions serves either to precipitate the polysaccharide preferentially to protein and nucleic acid contaminants, or in the reverse, preferentially precipitating contaminants. Those polysaccharides that precipitate may then be solubilized, in sodium chloride (usually 0.25 M) and centrifuged to remove contaminating macromolecules which are insoluble in the salt. Though the concentration of hexadecyltrimethylammonium bromide and salt may vary for optimal purificaton of the polysaccharide, this procedure has proven effective for types 1, 3, 4, 8, 12F, and 25 which are precipitated.

Eight types (6A, 6B, 7F, 9N, 14, 19F, 20, and 23F) are not precipitated by hexadecyltrimethylammonium bromide. In the case of these eight types, the hexadecyltrimethylammonium bromide is added and the resulting contaminant precipitate, separated by centrifugation, is discarded. Since hexadecyltrimethylammonium bromide is soluble in alcohol, subsequent alcohol precipitations are effective both in further purifying the polysaccharide and in removing residual hexadecyltrimethylammonium bromide. This general scheme is the broad procedure suitable with variations to a number of pneumococcal polysaccharide types. Type 3 and 18C are peculiar in not being purified through use of cetavlon.

After the treatment with alcohol which effectively removes the cetavlon, different steps may be incorporated for contaminants unique to specific strains. The pneumococcal polysaccharide can then be dialyzed, lyophilized and stored as a dry powder at −20° C. or lower.

A vaccine can be made by dissolving the polysaccharides in an appropriate buffer such as phosphate buffer containing a preservative followed by sterile filtration.

A common purification scheme for a pneumococcal polysaccharide can be summarized as follows:

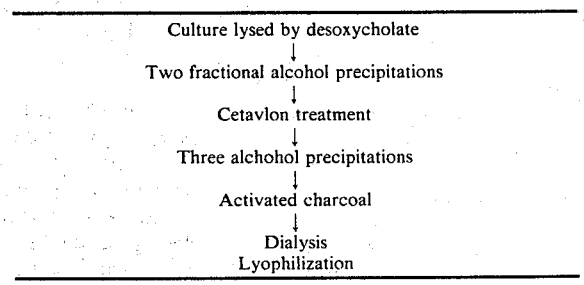

Culture lysed by desoxycholate
↓
Two fractional alcohol precipitations
↓
Cetavlon treatment
↓
Three alchohol precipitations
↓
Activated charcoal
↓
Dialysis
Lyophilization Table II shows the effectiveness of cetavlon in removing nucleic acid and protein contaminants from representative batches of pneumococcal polysaccharide.

It is an object of this invention to provide a highly purified effectively immunogenic multivalent pneumococcal polysaccharide vaccine substantially absent "C" polysaccharide contamination for types 1, 2, 3, 6A, 6B, 8, 9N, 12F, 18C, 19F, 20, 23F, and 25 pneumococcus.

It is a particular object of this invention to provide a highly immunogenic pneumococcal polysaccharide vaccine substantially absent "C" polysaccharide contamination for types 1, 2, 3, 4, 6A, 7F, 8, 9N, 12F, 14, 18C, 19F, 23F and 25.

It is another object of the present invention to provide a process for purifying immunologically active capsular polysaccharide of types 1, 2, 3, 6A, 6B, 8, 9N, 12F, 18C, 19F, 20, 23F and 25 pneumococcus.

It is a further object of this invention to provide a process for purifying immunologically active capsular polysaccharides of types 4, 7F, and 14 pneumococcus while being essentially free from "C" polysaccharide.

TABLE II

| Polysaccharide Type | Percent of Contaminant Removed by Cetavlon | |
|---|---|---|
| | Protein[1] | Nucleic Acid[2] |
| 1 | 92 | 96 |
| 2 | 50 | 58 |
| 4 | 79 | 75 |
| 6A | 0 | 57 |
| 6B | 74 | 82 |
| 7F | 51 | 83 |
| 8 | 94 | 99 |
| 9N | 33 | 70 |
| 12F | 60 | 79 |
| 14 | 80 | 94 |
| 19F | 55 | 69 |
| 20 | 8 | 17 |
| 23F | 44 | 64 |
| 25 | 65 | 89 |

[1]Protein determinations by method of Lowry, et al. just prior to and following Cetavlon treatment. Adjustments made for volume changes when necessary.
[2]Nucleic Acid determined by optical density in spectrophotometer at 260 millimicrons, prior to and following Cetavlon treatments. Adjustments made for volume changes when necessary.

DETAILED DESCRIPTION OF THE INVENTION

An effective multivalent pneumococcal vaccine absent "C" polysaccharide may be prepared by adding to a solution of 0.1 M phosphate buffer containing 0.01% thimerosal, sufficient lyophilized immunologically active pneumococcal polysaccharide to yield a final concentration of about 100 micrograms/ml/type. This is a generally effective amount as the exact concentration of polysaccharide to provide immunity exhibits variance with both the pneumococcal type and subject to be immunized.

This mixture is stirred about 4 hours at about 4° C. and sterile filtered. In one embodiment 1.0 mg each of lyphilized pneumococcal polysaccharide of types 1, 2, 3, 4, 6A, 6B, 7F, 8, 9N, 12F, 14, 18C, 19F, 20, 23F and 25 is combined with 0.1 M phosphate buffer containing 0.01% thimerosal to a final volume of 10 cc and stirred for about 4 hours at 4° C. Types 4, 7F, and 14 are added in a state essentially free* from "C" polysaccharide and exhibiting effective immunogenicity.
* less than 0.5% of "C" polysaccharide present.

In the preferred embodiment the above procedure is utilized but only 14 pneumococcal types are used. These types are types 1, 2, 3, 4, 6A, 7F, 8, 9N, 12F, 14, 18C, 19F, 23F and 25. Critical to the above preparations of an effective multivalent vaccine is the purification of each pneumococcal type utilized without loss of native state configuration and hence loss of effective immunogenicity. Of the ensuing examples, 16 will illustrate the specific methods of obtaining pure immunologically active polysaccharide from specific pneumococcus types. These types may be utilized for causing specific immunogenic response in warm-blooded animals or be utilized in combinations as multivalent vaccines. The two multivalent vaccines described above will be seen as merely illustrative of the many combinations of multivalent vaccines which may be prepared utilizing in whole or in part the 16 purified pneumococcal capsular polysaccharides of the present invention.

These examples are arranged in the following order:

| Examples | Danish Types | American Types |
|---|---|---|
| 1 | 1 | 1 |
| 2 | 2 | 2 |
| 3 | 4 | 4 |
| 4 | 8 | 8 |
| 5 | 12F | 12 |
| 6 | 25 | 25 |
| 7 | 6A | 6 |
| 8 | 6B | 26 |
| 9 | 7F | 51 |
| 10 | 9N | 9 |
| 11 | 14 | 14 |
| 12 | 19F | 19 |
| 13 | 20 | 20 |
| 14 | 23F | 23 |
| 15 | 3 | 3 |
| 16 | 18C | 56 |

Examples 1 to 6 are for types 1, 2, 4, 8, 12F, and 25 wherein the polysaccharide is precipitated by cetavlon, and then resuspended in 0.25 M NaCl (except Typ 4, 1 M NaCl). Examples 7 to 14 are for types 6A, 6B, 7F, 9N, 14, 19F, 20, 23F which are not precipitated by cetavlon but contaminants are precipitated. Examples 15 and 16 for types 3 and 18C are not treated with cetavlon. Note that types 6A, 6B, 9N, 19F, 20, and 23F require the presence of 0.15 M NaCl during cetavlon precipitation while the others are run in water.

EXAMPLE 1

Type 1 Pneumococcus

PREPARATION OF RAW POLYSACCHARIDE SUSPENSION

Three to five hundred liters of medium is used to grow Type 1 pneumococcus under conditions suitable for such growth to reach stationary phase. The bacteria are then lysed by the addition of a 10% sterile filtered solution of suitable lysant, herein sodium dexosycholate. Many methods of lysing such as other detergents and mechanical methods such as sonic disruption and French pressure cells may be used. All would produce fully equivalent material for the process of this invention. When sodium desoxycholate is used, a suitable lysing concentration has been found to be about 0.1-0.2%. All bacterial cells are lysed releasing cell associated polysaccharide into the medium. The turbid medium is clarified by centrifugation. Herein a model 16 Sharples centrifuge was used at 16,000 rpm and at a flowrate of 36-40 liters per hour while maintaining a temperature of about 2°-10° C. Cellular debris thus collected is discarded. The polysaccharide bearing supernatant is adjusted to a pH of about 6.6. In these examples pH adjustment was usually accomplished by the addition of 8 M acetic acid. It is important to note that the exact pH valves designated in the preliminary steps are general and indicative only of the preferred mode. Wide variance in the useful pH ranges is to be understood with all pneumococcal types. Only the precipitating steps utilizing cetavlon require a highly specific pH be observed. Similarly, acetic acid is merely illustrative of one acidifying agent. Acetic acid is preferred as permitting use of sodium acetate with an attendant buffering action but those skilled in the art will immediately understand that other pH adjusting systems of other acids, bases and buffers could easily be devised. The above prepares a raw polysaccharide supernatant for the purification process of this invention.

PURIFICATION OF THE POLYSACCHARIDE: TYPE 1

[A] First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.5 volumes and preferably 0.4 volumes, slowly with stirring at a temperature of 2°-6° C. The pH is adjusted to about 7.0, and in the preferred mode to ±0.1 with 8 M acetic acid. As the precipitate forms slowly the mixture is permitted to stand overnight, about 16-20 hours. As pneumococcal polysaccharides tend to be labile they are best handled at reduced temperatures, thus during the 16-20 hour period the polysaccharide bearing solution should be kept chilled, here about 4° C. The above-described fractionation scheme is standard for the alcohol precipitation steps in the pneumococcal polysaccharide purification. The variability of the above scheme for other types will reside primarily but not exclusively in the volumes of alcohol and the order of steps used with the specific types. The precipitated contaminants will uniformly be eliminated by centrifugation in the centrifuge at a flow rate of about 16-20 liters per hour while kept at a reduced temperature, the preferred temperature being from about 2° to about 6° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 1, alcohol is added from about 0.5 volume to about 1.0 volume minimum and the pH adjusted to 7. With Type 1 the preferred final alcohol concentration must exceed about 0.75 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°-6° C., and at a flow rate of about 6-7 liters per hour.

[B] Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.15 to 0.35 volumes is added, and in the preferred embodiment 0.25 volumes the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 0.5 to 1.0 volume is added to a final minimum concentration of 0.75 volumes in the preferred embodiment and the pH adjusted to 7. This is followed by standing, as in the first fractional alcohol precipitation centrifugation and again being redissolved in about 40 liters of cold pyrogen-free water, about 4° C. in the preferred embodiment.

[C] Hexadecyltrimethyl Ammonium Bromide (Cetavlon) Fractional Precipitation:

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 1.5 to 5.0 volumes percent* with the preferred concentration being 1.25 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 1 pneumococcal polysaccharide is precipitated by cetavlon along with some impurities. The precipitate is redissolved in 40 liters of about 0.25 M NaCl and stirred chilled, here about 4° C. The turbid suspension is centrifuged chilled, here at a flow rate of about 6-7 liters per hour and at 7°-12° C. The polysaccharide is now in solution while the nucleic acid and other impurities are in the centrifugation pellet, which may be discarded. This procedure removes 96% of the nucleic acid and 92% of the protein as measured against the material composition before cetavlon treatment.

The polysaccharide is then reprecipitated, the supernatant being adjusted to a pH of about 6.6 with sodium acetate to about 4%. The pH then raised to about 6.7 and about 1 volume of alcohol is added, the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

*Throughout this specification, concentrations of cetavlon will be expressed in values % based on a 10% cetavlon solution. It is to be understood that altering the concentration fo the cetavlon solution would correspondingly alter the amount of such solution added to reach an equivalent final concentration.

[D] Activated Charcoal Purification

The polysaccharide solution still chilled si then adjusted to a pH of about 6.1 with 0.3 M acetic acid and sodium chloride to a 0.15 M concentration. A 20% suspension of activated charcoal is added with stirring to result in a 3 to 7% concentration of activated charcoal with 5% being preferred*. The mixture is permitted to stand chilled, about 4° C., for about 30 minutes. This mixture is filtered to remove activated charcoal and further clarified by passage through a series of millipore type membranes. In the preferred embodiment a 293 mm Millipore housing containing a CPX-10C (AMF-CUNO pad) apparatus was used and 1.2, 0.65, 0.45 and 0.22 u millipore membrantes. During this procedure optical density at 260mu is monitored as a check on nucleic acid concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 1. This powder is harvested under low humidity into jars which are then tightly sealed and stored super cold, below −20° C. being found suitable.

The above process has removed more than 99% of contaminant protein and nucleic acid while retaining the immunogenicity of the product.

*Throughout this specification concentrations of activated charcoal will be expressed in volumes percent based on a 20% activated charcoal suspension. It is to be understood that altering the concentration of such suspension would correspondingly alter the amount of such suspension needed to reach an equivalent final concentration.

EXAMPLE 2

Type 2 Pneumococcus

PREPARATION OF RAW POLYSACCHARIDE SUSPENSION

The raw polysaccharide is prepared from a Type 2 fermentation broth lysate as in the manner described in Example 1 for Type 1.

PURIFICATION OF THE POLYSACCHARIDE: TYPE 2

[A] First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.75 volumes and preferably 0.5 volumes, slowly with stirring at a temperature of 2°-6° C. The pH is adjusted to about 7.0, and in the preferred mode to ±0.1, with 8 M acetic acid. As the precipitate forms slowly the mixture is permitted to stand overnight, about 16-20 hours and centrifuged. As pneumococcal polysaccharides tend to be labile they are best handled at reduced temperatures, thus during the 16-20 hour period the polysaccharide bearing solution should be kept about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 2, alcohol is added from about 1.0 volume to about 1.5 volume minimum and the pH adjusted to 7. With Type 2 the final preferred concentration must exceed about 1.25 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, of reduced temperature, about 4° C. being preferred. If turbidity is apparent, the solution may be clarified by centrifugation at a reduced temperature, about 2°-6° C., and at a flow rate of about 6-7 liters per hour.

[B] Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.75 volumes is added, and in the preferred embodiment 0.5 volumes, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.0 to 1.5 volume is added to a final minimum concentration of 1.25 volumes in the preferred embodiment and the pH adjusted to 7. This is followed by standing and centrifugation as in the first fractional alcohol precipitation, and again being redissolved in about 40 liters of cold pyrogen-free water, about 4° C. in the preferred embodiment.

[C] Hexadecyltrimethyl Ammonium Bromide (Cetavlon) Fractional Precipitation:

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring a 10% solution of cetavlon is added slowly to a concentration of 1.0 to 3.0 volumes percent with the preferred concentration being 2.0 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 2 pneumococcal polysaccharide is precipitated by cetavlon along with some impurities. The precipitate is redissolved in 40 liters of about 0.25 M NaCl and stirred chilled, here about 4° C. The turbid suspension is centrifuged chilled, here at a flow rate of about 6-7 liters per hour and at 7°-12° C. The polysaccharide is now in solution while the nucleic acid and other impurities are in the centrifugation pellet which may be discarded. This procedure removes 58% of the nucleic acid and 50% of the protein as measured against the material composition before cetavlon treatment.

The polysaccharide is then reprecipitated, the supernatant being adjusted to a pH of about 6.6 with sodium acetate to about 4%. The pH then raised to about 6.7 and about 1.25 volume of alcohol is added, and the pH adjusted to 7 at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

[D] Activated Charcoal Purification:

The polysaccharide solution still chilled is then adjusted to a pH of about 6.1 with 0.3 M acetic acid and sodium chloride to a 0.15 M concentration. A 20% suspension of activated charcoal is added with stirring to result in a 3 to 7% concentration of activated charcoal with 5% being preferred. The mixture is permitted to stand chilled, about 4° C., for about 30 minutes. This mixture is filtered to remove activated charcoal and further clarified by passage through a series of millipore type membranes. In the preferred embodiment a 293 mm Millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 2. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 3

Type 4 Pneumococcus

PREPARATION OF RAW POLYSACCHARIDE SUSPENSION

The raw polysaccharide is prepared from a Type 4 fermentation broth lysate as in the manner described in Example 1 for Type 1.

PURIFICATION OF THE POLSYACCHARIDE: TYPE 4

[A] First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.5 volumes to 1.0 volumes and preferably 0.75 volumes, slowly with stirring at a temperature of 2°-6° C. The pH is adjusted to about 7.0, and in the preferred mode to ±0.1, with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7. For Type 4, alcohol is added from about 2.25 volume to about 2.75 volume minimum and the pH adjusted to 7. With Type 4 the final preferred concentration must exceed about 2.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, at reduced temperature, about 4° C. being preferred. If turbidity is apparent, the solution may be clarified by centrifugation at a reduced temperature, about 2°-6° C., and at a flow rate of about 6-7 liters per hour.

[B] Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.75 to 1.25 volumes is added, and in the preferred embodiment 1.0 volume and the pH adjusted to 7 and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH is adjusted to about 6.7 as described in the first fractional alcohol precipitation and ±0.1 in the preferred embodiment. Alcohol from about 2.5 to 3.0 volume is added to a final minimum concentration of 2.5 volumes in the preferred embodiment and the pH adjusted to 7. This is followed by standing, as in the first fractional alcohol precipitation, centrifugation and again being redissolved in about 40 liters of cold pyrogen-free water, about 4° C. in the preferred embodiment.

[C] Hexadecyltrimethyl Ammonium Bromide (Cetavlon) Fractional Precipitation:

Thg polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 1.0 to 3.0 volumes percent with the preferred concentration being 2.0 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With the procedure Type 4 pneumococcal polysaccharide is precipitated by cetavlon along with some impurities. The precipitate is redissolved in 40 liters of about 1.0 M NaCl and stirred chilled, here about 4° C. The turbid suspension is centrifuged chilled, here at a flow rate of about 6–7 liters per hour and at 7°–12° C. The polysaccharide is now in solution while the nucleic acid and other impurities are in the centrifugation pellet which may be discarded. This procedure removes 75% of the nucleic acid and 79% of the protein as measured against the material composition before cetavlon treatment.

The polysaccharide is then reprecipitated, the supernatant being adjusted to a pH of about 6.6 with sodium acetate to about 4%. The pH is then raised to about 6.7 and about 1 volume of alcohol is added and the pH adjusted to 7 standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

[D] "C" Polysaccharide removal

Ammonium sulfate is slowly added to this solution at a pH of about 7.0 to a concentration of 25 to 45% and preferably about 35%. The mixture is permitted to stand until a precipitate forms. This is about 30 minutes at 4° C. The precipitate may then be removed by centrifugation at a flow rate of 2 to 3 liters/hour while chilled. The "C" polysaccharide and other impurities remain in the supernatant and are thus separated by centrifugation from the precipitated polysaccharide. This is redissolved in about 20 liters of water. Double immunodiffusion is employed using a "C" polysaccharide antiserum to assure the absence of "C" polysaccharide. The resultant product having less than 0.5% "C" polysaccharide is essentially free of this contaminant.

[E] Activated Charcoal Purification:

The polysaccharide solution still chilled is then adjusted to a pH of about 6.1 with 0.3 M acetic acid and sodium chloride to a 0.075 concentration. A 20% suspension of activated charcoal is added with stirring to result in a 1 to 3% concentration of activated charcoal with 2% being preferred. The mixture is permitted to stand chilled, about 4° C., for about 30 minutes. This mixture is filtered to remove activated charcoal and further clarified by passage through a series of millipore type membranes. In the preferred embodiment a 293 mm Millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 4. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 4

Type 8 Pneumococcus

PREPARATION OF RAW POLYSACCHARIDE SUSPENSION

The raw polysaccharide is prepared from a Type 8 fermentation broth lysate as in the manner described in Example 1.

PURIFICATION OF THE POLYSACCHARIDE: TYPE 8

[A] First Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.75 volumes and preferably 0.5 volumes, slowly with stirring at a temperature of 2°–6° C. The pH is adjusted to about 7.0 and in the preferred mode to ±0.1, with 8 M acetic acid. As the precipitate, here polysaccharide, forms slowly the mixture is permitted to stand overnight, about 16–20 hours. As pneumococcal polysaccharides tend to be labile they are best handled at reduced temperatures, thus during the 16–20 hour period the polysaccharide bearing fraction should be kept chilled, here about 4° C. THe polysaccharide precipitate is dissolved with stirring in sufficient water, usually about 40 liters, at reduced temperature, about 4° C. being preferred. If turbidity is apparent, the solution may be clarified by centrifugation at a reduced temperature, about 2°–6° C., and at a flow rate of about 6–7 liters per hour.

[B] Second Alcohol Precipitation

This is performed as in the first alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.5 to 1.0 volumes is added and the pH adjusted to 7, and in the preferred embodiment 0.75 volumes, and treated as described in the first alcohol precipitation with stirring chilled, pH adjustment, standing and clarification through centrifugation. The polysaccharide precipitate redissolved in about 40 liters of cold pyrogen-free water, about 4° C. in the preferred embodiment.

[C] Hexadecyltrimethyl Ammonium Bromide (Cetavlon) Fractional Precipitation:

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 3.0 to 5.0 volumes percent with the preferred concentration being 4.0 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 8 pneumococcal polysaccharide is precipitated by cetavlon along with some impurities. The precipitate is redissolved in 40 liters of about 0.25 M NaCl and stirred chilled, here about 4° C. The turbid suspension is centrifuged chilled, here at a flow rate of about 6-7 liters per hour and at 7°-12° C. The polysaccharide is now in solution while the nucleic acid and other impurities are in the centrifugation pellet which may be discarded. This procedure removes 99% of the nucleic acid and 94% of the protein as measured against the material composition before cetavlon treatment.

The polysaccharide is then reprecipitated, the supernatant being adjusted to a pH of about 6.6 with sodium acetate to about 4%. The pH then raised to about 6.7 and about 0.75 volumes of alcohol is added and the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

[D] Activated Charcoal Purification:

The polysaccharide solution still chilled is then adjusted to a pH of about 6.1 with 0.3 M acetic acid and sodium chloride to a 0.6 M concentration. A 20% suspension of activated charcoal is added with stirring to result in a 2 to 6% concentration of activated charcoal with 4% being preferred. The mixture is permitted to stand chilled, about 4° C., for about 30 minutes. This mixture is filtered to remove activated charcoal and further clarified by passage through a series of millipore type membranes. In the preferred embodiment a 293 mm Millipore housing containing a CPX-10C (AMF-CUNO pad) apparatus was used and 1.2, 0.65, 0.45 and 0.22u millipore membranes. During this procedure optical density at 260 MU is monitored as a check on nucleic acid and concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 8. This powder is harvested under low humidity into jars which are then tightly sealed and stored super cold, below 20° C. being found suitable.

The above process has removed more than 99% of contaminant protein and nucleic acid while retaining the immunogenicity of the product.

EXAMPLE 5

Type 12F Pneumococcus

PREPARATION OF RAW POLYSACCHARIDE SUSPENSION

The raw polysaccharide is prepared from a type 6A fermentation broth lysate as in the manner described in Example 1.

[A] First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.55 volumes and preferably 0.4 volumes, slowly with stirring at a temperature of 2°-6° C. The pH is adjusted to about 7.0 and in the preferred mode to ±0.1, with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate is added to a concentration of 4% as against the final volume when the alcohol of the next step is added and the pH is then rasied to about 6.7 and, for Type 12F, alcohol is added from about 0.75 volume to about 1.25 volume minimum and the pH adjusted to 7. With Type 12F the preferred final concentration must exceed about 1.0 volumes for total polysaccharide precipitation.

The mixture is then allowed to stand at a reduced temperature and for a comparable time as in the first alcohol fractional precipitation and is similarly centrifuged; however, this is the polysacchride precipitated in this step. The polysaccharide precipitate is dissolved with stirring in sufficient water, usually about 40 liters, at reduced temperature, about 4° C. being preferred. If turbidity is apparent, the solution may be clarified by centrifugation at a reduced temperature, about 2°-6° C., and at a flow rate of about 6-7 liters per hour.

[B] Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.55 volumes is added, and the pH adjusted to 7 and in the preferred embodiment 0.4 volumes, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 0.75 to 1.25 volume is added to a final minimum concentration of 1.0 volumes in the preferred embodiment and the pH adjusted to 7. This is followed by standing, as in the first fractional alcohol precipitation centrifugation and again beinf redissolved in about 40 liters of cold pyrogen-free water, about 4° C. in the preferred embodiment.

[C] Hexadecyltrimethyl Ammonium Bromide (Cetavlon) Fractional Precipitation:

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 1.0 to 3.5 volumes percent with the preferred concentration being 2.0 volumes percent. After standing until the precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 12F pneumococcal polysaccharide is precipitated by cetavlon along with some impurities. The precipitate is redissolved in 40 liters of about 0.25 M NaCl and stirred chilled, here about 4° C. The turbid suspension is centrifuged chilled, here at a flow rate of about 6-7 liters per hour and at 7°-12° C. The polysaccharide is now in solution while the nucleic acid and other impurities are in the centrifugation pellet which may be discarded. This procedure removes 79% of the nucleic acid and 60% of the protein as measured against the material composition before cetavlon treatment.

The polysaccharide is then reprecipitated, the supernatant being adjusted to a pH of about 6.6 and sodium acetate added to about 4%. The pH then raised to about 6.7 and about 1.25 volumes of alcohol is added and the pH adjusted to 7 at abour 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

[D] Activated Charcoal Purification

The polysaccharide solution still chilled is then adjusted to a pH of about 6.1 with 0.3 M acetic acid and sodium chloride to a 0.14 M concentration. A 20% suspension of activated charcoal is added with stirring to result in a 1.0 to 5.0% concentration of activated charcoal with 3.0% being preferred. The mixture is permitted to stand chilled, about 4° C., for about 30 minutes. This mixture is filtered to remove activated charcoal and further clarified by passage through a series of millipore type membranes. In the preferred embodiment a 293 mm Millipore housing containing a CPX-10C (AMF-CUNO pad) apparatus was used and 1.2, 0.65, 0.45 and 0.22u millipore membranes. During this procedure optical density at 260 MU is monitored as a check on nucleic acid and concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 12F. This powder is harvested under low humidity into jars which are then tightly sealed and stored super cold, below −20° C. being found suitable.

The above process has removed moe than 99% of contaminant protein and nucleic acid while retaining the immunogenicity of the product.

EXAMPLE 6

Type 25 Pneumococcus

PREPARATION OF RAW POLYSACCHARIDE SUSPENSION

The raw polysaccharide is prepared from a type 25 fermentation broth lysate as in the manner described in Example 1.

PURIFICATION OF THE POLYSACCHARIDE: TYPE 25

[A] First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.75 volumes and preferably 0.5 volumes, slowly with stirring at a temperature of 2°-6° C. The pH is adjusted to about 7.0 and in the preferred mode to ±0.1, with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 25, alcohol is added from about 1.25 volume to about 1.75 volume minimum and the pH adjusted to 7. With Type 25 the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, at reduced temperature, about 4° C. being preferred. If turbidity is apparent, the solution may be clarified by centrifugation at a reduced temperature, about 2°-6° C., and at a flow rate of about 6-7 liters per hour.

[B] Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.75 volumes is added and the pH adjusted to 7 and in the preferred embodiment 0.5 volumes, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.5 to 2.0 volume is added to a final minimum concentration of 1.75 volumes in the preferred embodiment and the pH adjusted to 7. This is followed by standing, as in the first fractional alcohol precipitation, centrifugation, and again being redissolved in about 40 liters of cold pyrogen-free water, about 4° C. in the preferred embodiment.

[C] Hexadecyltrimethyl Ammonium Bromide (Cetavlon) Fractional Precipitation:

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 4.0 to 8.0 volumes percent with the preferred concentration being 6.0 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 25 pneumococcal polysaccharide is precipitated by cetavlon along with some impurities. The precipitate is redissolved in 40 liters of about 0.25 M NaCl and stirred chilled, here about 4° C. The turbid suspension is centrifuged chilled, here at a flow rate of about 6–7 liters per hour and at 7°–12° C. The polysaccharide is now in solution while the nucleic acid and other impurities are in the centrifugation pellet which may be discarded. This procedure removes 89% of the nucleic acid and 65% of the protein as measured against the material composition before cetavlon treatment.

The polysaccharide is then reprecipitated, the supernatant being adjusted to a pH of about 6.6 and sodium acetate added to about 4%. The pH is adjusted to about 6.7 and about 1.75 volumes of alcohol is added and the pH adjusted to 7 standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

[D] Activated Charcoal Purification:

The polysaccharide solution still chilled is then adjusted to a pH of about 6.1 with 0.3 M acetic acid and sodium chloride to a 0.15 M concentration. A 20% suspension of activated charcoal is added with stirring to result in a 5 to 9% concentration of activated charcoal with 7% being preferred. The mixture is permitted to stand chilled, about 4° C., for about 30 minutes. This mixture is filtered to remove activated charcoal and further clarified by passage through a series of millipore type membranes. In the preferred embodiment a 293 mm Millipore housing containing a CPX-10C (AMF-CUNO pad) apparatus was used and 1.2, 0.65, 0.45 and 0.22u millipore membranes. During this procedure optical density at 260 MU is monitored as a check on nucleic acid and concentration and the method of Lowry et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 25. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 7

Type 6A Pneumococcus

PREPARATION OF RAW POLYSACCHARIDE SUSPENSION

The raw polysaccharide is prepared from a type 6A fermentation broth lysate as in the manner described in Example 1.

PURIFICATION OF THE POLYSACCHARIDE: TYPE 6A (A) First Fractional Alcohol Precipitation To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.4 volumes to 0.6 volumes and preferably 0.5 volumes, slowly with stirring at a temperature of 2°–6° C. The pH is adjusted to about 7.0, and in the preferred mode to ±0.1 with 8 M acetic acid. As the precipitate forms slowly the mixture is permitted to stand overnight, about 16–20 hours, and centrifuged. As pneumococcal polysaccharides tend to be labile they are best handled at reduced temperature, thus during the 16–20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and, for Type 6A, alcohol is added from about 1.25 volume to about 1.75 volume minimum and the pH adjusted to 7. With Type 6A the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, at a reduced temperature, about 4° C. being preferred. If turbidity is apparent, the solution may be clarified by centrifugation at a reduced temperature, about 2°–6° C., and at a flow rate of about 6–7 liters per hour.

[B] Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.4 to 0.6 volumes is added, the pH adjusted to 7 and in the preferred embodiment 0.5 volumes, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6, and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.25 to 1.75 volume is added with a preferred final minimum concentration of 1.5 volumes in the preferred embodiment and the pH adjusted to 7. This is followed by standing, as in the first fractional alcohol precipitation, centrifugation and again the precipitant being redissolved in about 40 liters of cold pyrogen-free water, about 4° C. in the preferred embodiment.

(C) Third Fractional Alcohol Precipitation

A third fractional alcohol precipitation is begun by adjusting the solution of redissolved precipitant to a pH of about 6.6 with ±0.1 being preferred. Sodium acetate is added to a 4% final concentration and the pH adjusted to 6.7 with ±0.1 preferred. Between 0.5 and 1.0 volumes alcohol are added with 0.75 being preferred and the pH adjusted to 7. This fractional precipitation is treated as in the first two fractional precipitations described above.

The supernatant is then adjusted to a pH of 6.7 ±0.1 and sodium acetate added to 4% concentration and 1.25 to 1.75 volumes of alcohol added with 1.5 volumes being preferred and the pH adjusted to 7.

This is again followed by standing, centrifugation and redissolution in about 40 liters of cold pyrogen-free water.

(D) Hexadecyltrimethyl Ammonium Bromide (Cetavlon) Fractional Precipitation:

The polysaccharide solution is then allowed to warm to room temperature (21° C. to 25° C.) and the pH is adjusted to 7.4 ±0.1 with sodium carbonate in solution. A concentration of 0.4% sodium carbonate has been found to be convenient for this adjustment solution.

Sodium chloride to 0.15 M is added and with stirring, a 10% solution of cetavlon is added slowly to a concentration of 0.05 to 0.2 volumes percent with the preferred concentration being 0.1 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure Type 6A pneumococcal polysaccharide is not precipitated by cetavlon. The precipitate is discarded. The polysaccharide is now in solution while the nucleic acid and other impurities are in the centrifugation pellet, which may be discarded. This procedure removes 57% of the nucleic acid as measured against the material composition before cetavlon treatment.

The supernatant bearing the polysaccharide is then reprecipitated, the supernatant being adjusted to a pH of about 6.6 and sodium acetate added to about 4%. The pH then raised to about 6.7 and about 1.5 volume of alcohol is added and the pH adjusted to 7, standing at about 4° C. for 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(E) Activated Charcoal Purification

The polysaccharide solution still chilled is then adjusted to a pH of about 6.1 with 0.3 M acetic acid and sodium chloride to a 0.15 M concentration. A 20% suspension of activated charcoal is added with stirring to result in a 5 to 9% concentration of activated charcoal with 7% being preferred.* The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 mu is monitored as a check on nucleic acid concentration and the method of Lowry et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 6A. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 8

Type 6B Pneumococcus

PREPARATION OF RAW POLYSACCHARIDE SUSPENSION

The raw polysaccharide is prepared from a type 6B fermentation broth lysate as in the manner described in Example 1.

PURIFICATION OF THE POLYSACCHARIDE: TYPE 6B

(A) First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.4 volumes to 0.6 volumes and preferably 0.5 volumes, slowly with stirring at a temperature of 2°–6° C. The pH is adjusted to about 7.0, and in the preferred mode to ±0.1 with 8 M acetic acid. As the precipitate forms slowly the mixture is permitted to stand overnight, about 16–20 hours, and centrifuged. As pneumococcal polysaccharides tend to be labile they are best handled at reduced temperatures, thus during the 16–20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 6B, alcohol is added from about 1.25 volume to about 1.75 volume minimum and the pH adjusted to 7. With Type 6B the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.15 to 0.35 volumes is added, and the pH adjusted to 7, and in the preferred embodiment 0.25 volumes, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.25 to 1.75 volume is added to a final minimum concentration of 1.5 volumes in the preferred embodiment and the pH adjusted to 7. This is followed by standing, as in the first fractional alcohol precipitation centrifugation and again being redissolved in about 40 liters of cold pyrogen-free water, about 4° C. in the preferred embodiment.

(C) Third Fractional Alcohol Precipitation

A third fractional alcohol precipitation is begun by adjusting the solution of redissolved precipitate to a pH of about 6.6 with ±0.1 being preferred. Sodium acetate is added to a 4% final concentration and the pH adjusted to 6.7 with ±0.1 preferred. Between 0.25 and 0.75 volumes alcohol are added with 0.5 being preferred and the pH adjusted to 7. This fractional precipitation is treated as in the first two fractional precipitations described above.

The supernatant is then adjusted to a pH of 6.7 ±0.1 and sodium acetate added to 4% concentration and 1.25 to 1.75 volumes of alcohol added with 1.5 volumes being preferred and the pH adjusted to 7.

This is again followed by standing, centrifugation, and redissolutions in about 40 liters of cold pyrogen-free water.

(D) Hexadecyltrimethyl Ammonium Bromide (Cetavlon) Fractional Precipitation

The polysaccharide solution is then allowed to warm to room temperature (21° C. to 25° C.) and the pH is adjusted to 7.4 ±0.1 with sodium carbonate in solution. A concentration of 0.4% sodium carbonate has been found to be convenient for this adjustment solution.

Sodium chloride to 0.15 M concentration is added and with stirring, a 10% solution of cetavlon is added slowly to a concentration of 0.3 to 0.5 volumes percent with the preferred concentration being 0.4 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure Type 6B pneumococcal polysaccharide is not precipitated by cetavlon. The precipitate is discarded. The polysaccharide is now in solution while the nucleic acid and other impurities are in the centrifugation pellet, which may be discarded. This procedure removes 82% of the nucleic acid and 74% of the protein as measured against the material composition before cetavlon treatment.

The supernatant bearing the polysaccharide is then reprecipitated, the supernatant being adjusted to a pH of about 6.6 with sodium acetate to about 4%. The pH then raised to about 6.7 and about 1.5 volume of alcohol is added the pH adjusted to 7, standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(E) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 6 to 10% concentration of activated charcoal with 8% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 6B. This powder is harvested under low humidity into jars which are then tightly sealed and stored super cold, below −20° C. being found suitable.

The above process has removed more than 99% of con-aminant protein and nucleic acid while retaining the immunogenicity of the product.

EXAMPLE 9

Type 7F Pneumococcus

PREPARATION OF RAW POLYSACCHARIDE SUSPENSION

The raw polysaccharide is prepared from a Type 7F fermentation broth lysate as in the manner described in Example 1.

PURIFICATION OF THE POLYSACCHARIDE: TYPE 7F (A) First Fractional Alcohol Precipitation To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.75 volumes to 1.25 volumes and preferably 1.0 volumes slowly with stirring at a temperature of 2°–6° C. The pH is adjusted to about 7.0, and in the preferred mode to ±0.1 with 8 M acetic acid. As the precipitate forms slowly the mixture is permitted to stand overnight, about 16–20 hours, and centrifuged. As pneumococcal polysaccharides tend to be labile they are best handled at reduced temperatures, thus during the 16–20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 7F, alcohol is added from about 2.5 volume to about 3.0 volume minimum and the pH adjusted to 7. With Type 7F the preferred final concentration must exceed about 2.75 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.75 to 1.25 volumes is added, the pH adjusted to 7, and in the preferred embodiment 1.0 volumes, and treated as described in the first fractional alcohol precipitation with stirring chilled, pH adjustment, standing and clarification through centrifugation. The precipitation thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 2.25 to 2.75 volume is added to a final minimum concentration of 2.5 volumes in the preferred embodiment, and the pH adjusted to 7. This is followed by standing, as in the first fractional alcohol precipitation centrifugation and again being redissolved in about 40 liters of cold pyrogen-free water, about 4° C. in the preferred embodiment.

(C) Hexadecyltrimethyl Ammonium Bromide (Cetavlon) Fractional Precipitation

The polysaccharide solution is then allowed to warm to room temperature (21° C. to 25° C.) and the pH is adjusted to 7.4 ±0.1 with sodium carbonate in solution. A concentration of 0.4% sodium carbonate has been found to be convenient for this adjustment solution.

With stirring, a 10% solution of cetavlon is added slowly to a concentration of 0.02 to 1.5 volumes percent with the preferred concentration being 0.075 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure Type 7F pneumococcal polysaccharide is not precipitated by cetavlon. The precipitate is discarded. The polysaccharide is now in solution while the nucleic acid and other impurities are in the centrifugation pellet, which may be discarded. This procedure removes 83% of the nucleic acid and 51% of the protein as measured against the material composition before cetavlon treatment.

The supernatant bearing the polysaccharide is then reprecipitated, the supernatant being adjusted to a pH of about 6.6 with sodium acetate to about 4%. The pH then raised to about 6.7 and about 2.75 volumes of alcohol is added, the pH adjusted to 7 standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) "C" Polysaccharide Removal

Ammonium sulfate is slowly added to this solution at a pH of about 7.0 to a concentration of 35 to 60% and preferably about 50%. The mixture is permitted to stand until a precipitate forms. This is about 30 minutes at 4° C. The precipitate may then be removed by centrifugation at a flow rate of 2 to 3 liters/hour while chilled. The "C" polysaccharide and other impurities remains in the supernatant and is thus separated from the precipitated polysaccharide. This is redissolved in about 20 liters of water. Double immunodiffusion is employed using a "C" polysaccharide antiserum to assure the absence of "C" polysaccharide. The resultant product is essentially free from "C" polysaccharide having less than 0.5% "C" polysaccharide.

(E) Activated Charcoal Purification

The polysaccharide solution, still chilled, is then adjusted to a pH of about 6.1 with 0.3 M acetic acid. A 20% suspension of activated charcoal is added with stirring to result in a 1.0 to 3.0% concentration of activated charcoal with 2% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 7F. This powder is harvested under low humidity into jars which are then tightly sealed and stored super cold, below 20° C. being found suitable.

The above process has removed more than 99% of contaminant protein and nucleic acid while retaining the immunogenicity of the product.

EXAMPLE 10

Type 9N Pneumococcus

PREPARATION OF RAW POLYSACCHARIDE SUSPENSION

The raw polysaccharide is prepared from a Type 9N fermentation broth lysate as in the manner described in Example 1.

PURIFICATION OF THE POLYSACCHARIDE: TYPE 9N (A) First Fractional Alcohol Precipitation To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.5 volumes to 1.0 volumes and preferably 0.75 volumes, slowly with stirring at a temperature of 2°-6° C. The pH is adjusted to about 7.0, and in the preferred mode to ±0.1 with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 9N, alcohol is added from about 1.0 volume to about 1.5 volumes minimum and the pH adjusted to 7. With type 9N the preferred final concentration must exceed about 1.25 volumes for total polysaccharide precitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°-6° C., and at a flow rate of about 6-7 liters per hour.

(B) Second Fractional Alcohol Precipitation

This is performed a' in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.75 volumes is added, and the pH adjusted to 7, and in the preferred embodiment 0.5 volumes, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.0 to 1.5 volume is added to a final minimum concentration of 1.25 volumes in the preferred embodiment and the pH adjusted to 7. This is followed by standing, as in the first fractional alcohol precipitation centrifugation and again being redissolved in about 40 liters of cold pyrogen-free water, about 4° C. in the preferred embodiment.

(C) Hexadecyltrimethyl Ammonium Bromide (Cetavlon) Fractional Precipitation

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

Sodium chloride to 0.15 M concentration is added and with stirring, a 10% solution of cetavlon is added slowly to a concentration of 0.05 to 0.5 volumes percent with the preferred concentration being 0.1 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 9N pneumococcal polysaccharide is not precipitated by cetavlon. The precipitate is discarded. The polysaccharide is now in solution while the nucleic acid and other impurities are in the centrifugation pellet, which may be discarded. This procedure removes 70% of the nucleic acid and 33% of the protein as measured against the material composition before cetavlon treatment.

The supernatant bearing the polysaccharide is then reprecipitated, the supernatant being adjusted to a pH of about 6.6 and sodium acetate added to about 4%. The pH then raised to about 6.7 and about 1.25 volume of alcohol is added, and the pH adjusted to 7 standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution, still chilled, is then adjusted to a pH of about 6.1 with 0.3 M acetic acid. A 20% suspension of activated charcoal is added with stirring to result in a 2 to 6% concentration of activated charcoal with 4% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 mu is monitored as a check on nucleic acid concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 9N. This powder is harvested under low humidity into jars which are then tightly sealed and stored super cold, below $-20°$ C. being found suitable.

The above process has removed more than 99% of contaminant protein and nucleic acid while retaining the immunogenicity of the product.

EXAMPLE 11

Type 14 Pneumococcus

PREPARATION OF RAW POLYSACCHARIDE SUSPENSION

The raw polysaccharide is prepared from a Type 14 fermentation broth lysate as in the manner described in Example 1.

PURIFICATION OF THE POLYSACCHARIDE: TYPE 14

(A) First Fractional Alcohol Precipitation

To the raw polysaccharide supernatant sodium acetate is added to a final concentration of about 4% as against supernatant and alcohol. pH is adjusted to about 6.7 and in the preferred mode to $\pm 0.1$ with 8 M acetic acid. Alcohol is added from 0.1 volumes to 0.5 volumes and preferably 0.25 volumes, slowly with stirring at a temperature of 2°-6° C. The pH is adjusted to about 7.0, and in the preferred mode to $\pm 0.1$ with 8 M acetic acid. As the precipitate forms slowly the mixture is permitted to stand overnight, about 16–20 hours, and centrifuged. As pneumococcal polysaccharides tend to be labile they are best handled at reduced temperatures, thus during the 16–20 hour period of polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 14, alcohol is added from about 1.25 volume to about 1.75 volume minimum, and the pH adjusted to 7. With Type 14 the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°-6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment $\pm 0.1$ being accomplished with 8 M acetic acid. Sodium acetate is added to a final concentration of about 4% and the pH adjusted to about 6.7 and $\pm 0.1$ as above being preferred. Alcohol from about 0.2 to 0.6 volumes is added, and in the preferred embodiment 0.4 volumes, and the pH adjusted to 7, and treated as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment $\pm 0.1$. To fully precipitate the polysaccharide sodium acetate is added to about a 4% final concentration and the pH adjusted to about 6.7 as described in the first fractional alcohol precipitation and $\pm 0.1$ in the preferred embodiment. Alcohol from about 1.25 to 1.75 volume is added to a final minimum concentration of 1.5 volumes in the preferred embodiment and the pH adjusted to 7. This is followed by standing, as in the first fractional alcohol precipitation centrifugation and again being redissolved in about 40 liters of cold pyrogen-free water, about 4° C. in the preferred embodiment.

(C) Hexadecyltrimethyl Ammonium Bromide (Cetavlon) Fractional Precipitation:

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

With stirring, a 10% solution of cetavlon is added slowly to a concentration of 0.05 to 0.3 volumes percent with the preferred concentration being 0.1 volumes percent. After standing until precipitate forms, here about 90 minutes, the mixture is rechilled to about 4° C. and the precipitate removed by centrifugation. A flow rate of 6 to 8 liters per hour and a temperature of 7°-14° C. is used in the preferred embodiment, but these ranges are general. With this procedure Type 14 pneumococcal polysaccharide is not precipitated by cetavlon. The precipitate is discarded. The polysaccharide is now in solution while the nucleic acid and other impurities are in the centrifugation pellet, which may be discarded. This procedure removes 94% of the nucleic acid and 80% of the protein as measured against the material composition before cetavlon treatment.

(D) "C" Polysaccharide Removal

The supernatant bearing the polysaccharide is then reprecipitated, the supernatant being adjusted to a pH of about 6.6 with sodium acetate to about 4%. The pH then raised to about 6.7 and about 1.5 volumes of absolute methanol is added to precipitate Type 14 polysaccharide and not precipitate "C" polysaccharide. This is followed by standing at about 4° C. 16-20 hours and centrifuging down the polysaccharide which is again redissolved in pyrogen-free water, about 40 liters being suitable. This procedure is repeated twice more with 1.5 volumes of alcohol to further purify the polysaccharide and remove traces of cetavlon, the last precipitate being redissolved in about 20 liters of water. The resultant product is essentially free from "C" polysaccharide having less than 0.5% "C" polysaccharide.

(E) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 2 to 6% concentration of activated charcoal with 4% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 14. This powder is harvested under low humidity into jars which are then tightly sealed and stored super cold, below −20° C. being found suitable.

The above process has removed more than 99% of contaminant protein and nucdeic acid while retaining the immunogenicity of the product.

EXAMPLE 12

Type 19F Pneumococcus

PREPARATION OF RAW POLYSACCHARIDE SUSPENSION

The raw polysaccharide is prepared from a type 19F fermentation broth lysate as in the manner described in Example 1.

PURIFICATION OF THE POLYSACCHARIDE: TYPE 19F

(A) First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes of 0.75 volumes and preferably 0.5 volumes, slowly with stirring at a temperature of 2°-6° C. The pH is adjusted to about 7.0, and in the preferred mode to ±0.1 with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 19F, alcohol is added from about 1.25 volume to about 1.75 volume minimum and the pH adjusted to 7. With Type 19F the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.75 volumes is added, the pH adjusted to 7, and in the preferred embodiment 0.5 volumes, and treated as described in the first fractional alcohol precipitation with stirring chilled, pH adjustment, standing and clarification through centrifugation. The precipitation thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 0.25 to 0.75 volume is added to a final minimum concentration of 0.5 volumes in the preferred embodiment and the pH adjusted to 7. This is followed by standing, as in the first fractional alcohol precipitation centrifugation and again being redissolved in about 40 liters of cold pyrogen-free water, about about 4° C. in the preferred embodiment.

(C) Hexadecyltrimethyl Ammonium Bromide (Cetavlon) Fractional Precipitation

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

Sodium chloride to 0.15 M concentration is added and with stirring, a 10% solution of cetavlon is added slowly to a concentration of 0.05 to 0.4 volumes percent with the preferred concentration being 0.2 volumes percent. After standing until precipitate forms, here about 90 minutes, the mixture is rechilled to about 4° C. and the precipitate removed by centrifugation. A flow rate of 6 to 8 liters per hour and a temperature of 7°-14°

C. is used in the preferred embodiment, but these ranges are general. With this procedure Type 19F pneumococcal polysaccharide is not precipitated by cetavlon. The precipitate is discarded. The polysaccharide is now in solution while the nucleic acid and other impurities are in the centrifugation pellet, which may be discarded. This procedure removes 69% of the nucleic acid and 55% of protein as measured against the material composition before cetavlon treatment.

The supernatant bearing the polysaccharide is then precipitated, the supernatant being adjusted to a pH of about 6.6 and sodium acetate added to about 4%. The pH then raised to about 6.7 and about 1.75 volume of alcohol is added and the pH adjusted to 7, standing at about 4° C. 16-20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 3 to 7% concentration with 5% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 19F. Prior to lyophilization, 0.01 to 25% glycine is added to the diafiltrate with 0.2% as the preferred amount. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 13

Type 20 Pneumococcus

PREPARATION OF RAW POLYSACCHARIDE SUSPENSION

The raw polysaccharide is prepared from a type 20 fermentation broth lysate as in the manner described in Example 1.

PURIFICATION OF THE POLYSACCHARIDE: TYPE 20

(A) First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.75 volumes and preferably 0.5 volumes, slowly with stirring at a temperature of 2°-6° C. The pH is adjusted to about 7.0, and in the preferred mode to ±0.1 with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 20, alcohol is added from about 1.25 volume to about 1.75 volume minimum and the pH adjusted to 7. With Type 25 the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.75 volumes is added, the pH adjusted to 7, and in the preferred embodiment 0.5 volumes, and treated as described in the first fractional alcohol precipitation with stirring chilled, pH adjustment, standing and clarification through centrifugation. The precipitation thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 0.25 to 1.75 volume is added to a final minimum concentration of 1.5 volumes in the preferred embodiment and the pH adjusted to 7. This is followed by standing, as in the first fractional alcohol precipitation centrifugation and again being redissolved in about 40 liters of cold pyrogen-free water, about 4° C. in the preferred embodiment.

(C) Third Fractional Alcohol Precipitation

A third fractional alcohol precipitation is begun by adjusting the solution of redissolved precipitate to a pH of about 6.6 with ±0.1 being preferred. Sodium acetate is added to a 4% final concentration and the pH adjusted to 6.7 with ±0.1 preferred. Between 0.5 and 1.0 volumes alcohol are added with 0.75 being preferred and the pH adjusted to 7. This fractional precipitation is treated as in the first two fractional precipitations described above.

The supernatant is then adjusted to a pH of 6.7±0.1 and sodium acetate added to 4% concentration and 1.25 to 1.75 volumes of alcohol added with 1.5 volumes being preferred, and the pH adjusted to 7.

This is again followed by standing, centrifugation, and redissolutions in about 40 liters of cold pyrogen-free water.

(D) Hexadecyltrimethyl Ammonium Bromide (Cetavlon) Fractional Precipitation

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

Sodium chloride to 0.15 M concentration is added and with stirring, a 10% solution of cetavlon is added slowly to a concentration of 0.1 to 0.5 volumes percent with the preferred concentration being 0.25 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure Type 20 pneumococcal polysaccharide is not precipitated by cetavlon. The precipitate is discarded. The polysaccharide is now in solution while the nucleic acid and other impurities are in the centrifugation pellet, which may be discarded. This procedure removes 17% of the nucleic acid and 8% of the protein as measured against the material composition before cetavlon treatment.

The supernatant bearing the polysaccharide is then reprecipitated the supernatant being adjusted to a pH of about 6.6 with sodium acetate to about 4%. The pH then raised to about 6.7 and about 1.5 volume of alcohol is added, and the pH adjusted to 7, standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(E) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 3 to 7% concentration of activated charcoal with 5% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 20. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 14

Type 23F Pneumococcus

PREPARATION OF RAW POLYSACCHARIDE SUSPENSION

The raw polysaccharide is prepared from a Type 23F fermentation broth lysate as in the manner described in Example 1.

PURIFICATION OF THE POLYSACCHARIDE: TYPE 23F (A) First Fractional Alcohol Precipitation To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.75 volumes and preferably 0.5 volumes, slowly with stirring at a temperature of 2°–6° C. The pH is adjusted to about 7.0, and in the preferred mode to ±0.1 with 8 M acetic acid. As the precipitate forms slowly the mixture is permitted to stand overnight, about 16–20 hours, and centrifuged. As pneumococcal polysaccharides tend to be labile they are best handled at reduced temperatures, thus during the 16–20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 23F, alcohol is added from about 1.0 volume to about 1.5 volume minimum. With Type 23F the preferred final concentration must exceed about 1.25 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°–6° C., and at a flow rate of about 6–7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.75 volumes is added, and in the preferred embodiment 0.5 volumes, and the pH adjusted to 7, as described in the first fractional alcohol precipitation with stirring chilled, pH adjustment, standing and clarification through centrifugation. The precipitate thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.0 to 1.5 volume is added to a final minimum concentration of 1.25 volumes in the preferred embodiment, and pH adjusted to 7 standing, centrifugation, and again being redissolved in about 40 liters of cold pyrogen-free water, about 4° C. in the preferred embodiment.

(C) Hexadecyltrimethyl Ammonium Bromide (Cetavlon) Fractional Precipitation

The polysaccharide solution is then allowed to warm to room temperature (21° C. to 25° C.) and the pH is adjusted to 7.4±0.1 with sodium carbonate in solution. A concentration of 0.4% sodium carbonate has been found to be convenient for this adjustment solution.

Sodium chloride to 0.15 M concentration is added and with stirring, a 10% solution of cetavlon is added slowly to a concentration of 0.1 to 0.3 volumes percent with the preferred concentration being 0.2 volumes percent. After standing until precipitate forms, here about 90 minutes, the mixture is rechilled to about 4° C. and the precipitate removed by centrifugation. A flow rate of 6 to 8 liters per hour and a temperature of 7°–14° C. is used in the preferred embodiment, but these ranges are general. With this procedure Type 2[F. pneumococcal polysaccharide is not precipitated by cetavlon. The precipitate is discarded. The polysaccharide is now in solution while the nucleic acid and other impurities are in the centrifugation pellet, which may be discarded. This procedure removes 64% of the nucleic acid and 44% of the protein as measured against the material composition before cetavlon treatment.

The supernatant bearing the polysaccharide is then reprecipitated, the supernatant being adjusted to a pH of about 6.6 and sodium acetate added to about 4%. The pH then raised to about 6.7 and about 1.25 volume of alcohol is added, the pH adjusted to 7, standing at about 4° C. 16–20 hours and centrifuging down the polysaccharide which is again redissolved in pyrogen-free water, about 40 liters being suitable. This procedure is repeated twice more to further purify the polysaccharide and remove traces of cetavlon, the last precipitate being redissolved in about 20 liters of water.

(D) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 2 to 6% concentration of activated charcoal with 4% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45 and 0.22u millipore membranes. During this procedure optical density at 260 MU is monitored as a check on nucleic acid concentration and the method of Lowry et al. is used to monitor protein content.

The resultant filtrate is warmed to room temperature, around 21°–25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 23F. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 15

Type 3 Pneumococcus

PREPARATION OF RAW POLYSACCHARIDE SUSPENSION

The raw polysaccharide is prepared from a Type 3 fermentation broth lysate as in the manner described in Example 1.

PURIFICATION OF THE POLYSACCHARIDE: TYPE 3

(A) First Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.15 volumes to 0.5 volumes and preferably 0.25 volumes, slowly with stirring at a temperature of 2°–6° C. The pH is adjusted to about 7.0, and in the preferred mode to ±0.1 with 8 M acetic acid. As the polysaccharide precipitate forms slowly the mixture is permitted to stand overnight, about 16–20 hours, and centrifuged. As pneumococcal polysaccharides tend to be labile they are handled at reduced temperatures, thus during the 16–20 hour period the polysaccharide precipitate should be kept chilled, here about 4° C. The polysaccharide precipitate is dissolved with stirring in sufficient 4% sodium acetate solution, usually about 320 liters, reduced temperature, about 4° C. being preferred. Brief mechanical agitation in a blender (4 to 6 seconds) aids this dissolution. If turbidity is apparent, the solution may be clarified by centrifugation at a reduced temperature, about 2°–6° C., and at a flow rate of about 16–18 liters per hour.

(B) Second Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.25 to 0.6 volumes is added, and in the preferred embodiment 0.4 volumes, the pH adjusted to 7 and treated as described in the first alcohol precipitation with stirring chilled, pH adjustment, standing and clarification through centrifugation. The polysaccharide precipitate thus removed, is redissolved in 100 liters of water and the water removed by lyophilization. The dry powder is redissolved in 1000 liters of water and centrifuged to remove turbidity. The supernatant is filtered using a Niagra filter press loaded with CPX 10C and CPX 70C pads (AMF CUNO). The partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first alcohol precipitation and ±0.1 in the preferred embodiment and alcohol from about 0.1 to 0.5 volume is added to a final minimum concentration of 0.5 volumes in the preferred embodiment in the pH adjusted to 7. This is followed by standing, as in the first alcohol precipitation centrifugation and again being redissolved in about 200 liters of cold pyrogen-free water, about 4° C. in the preferred embodiment.

(C) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 0.1 to 5% concentration of activated charcoal with 3% being preferred. The mixture is permitted to stand chilled, about 4° C., for about 30 minutes. This mixture is filtered to remove activated charcoal and further clarified by passage through a series of millipore type membranes. In the preferred embodiment of a 293 mm millipore housing containing a CPX-10C (AMF-CUNO pad) apparatus was used and 1.2, 0.65, 0.45 and 0.22 u millipore membranes. During this procedure optical density at 260 MU is monitored as a check on nucleic acid concentration and the method of Lowry et al. is used to monitor protein content.

The resultant filtrate is warmed to room temperature, around 21°-25° C., prior to dialysis. Here using Visking cellulose casings with a 10,000 M.W. cut off, and all residual sodium chloride removed. The dialyzed polysaccharide is then quick frozen, and lyophilized leaving purified pneumococcal polysaccharide powder, herein of Type 3. This powder is harvested under low humidity into jars which are then tightly sealed and stored super cold, below −20° C. being found suitable.

The above process has removed more than 99% of contaminant protein and nucleic acid while retaining the immunogenicity of the product.

EXAMPLE 16

Type 18C Pneumococcus

PREPARATION OF RAW POLYSACCHARIDE SUSPENSION

The raw polysaccharide is prepared from a type 18C fermentation broth lysate as in the manner described in Example 1.

PURIFICATION OF THE POLYSACCHARIDE: TYPE 18C

(A) First Fractional Alcohol Precipitation

To the raw polysaccharide supernatant sodium acetate is added to a final concentration of about 4% as against supernatant and alcohol. pH is adjusted to about 6.7 and in the preferred mode to ±0.1 with 8 M acetic acid. Alcohol is added from 0.25 volumes to 0.75 volumes and preferably 0.5 volumes, slowly with stirring at a temperature of 2°-6° C. The pH is adjusted to about 7.0, and in the preferred mode to ±0.1 with 8 M acetic acid. As the precipitate forms slowly the mixture is permitted to stand overnight, about 16-20 hours, and centrifuged. As pneumococcal polysaccharides tend to be labile they are best handled at reduced temperatures, thus during the 16-20 hour period the polysaccharide bearing solution should be kept chilled, here about 4° C.

The supernatant bearing the partially purified polysaccharide is adjusted to a pH of about 6.6 as above and sodium acetate added to a concentration of 4% as against the final volume when the alcohol of the next step is added and the pH is then raised to about 6.7 and for Type 18C, alcohol is added from about 1.25 volume to about 1.75 volume minimum, and the pH adjusted to 7. With Type 18C the preferred final concentration must exceed about 1.5 volumes for total polysaccharide precipitation.

The mixture is then allowed to stand at a reduced temperature and for a comparable time as in the first alcohol fractional precipitation and is similarly centrifuged; however, this is the polysaccharide precipitated in this step. The polysaccharide precipitate is dissolved with stirring in sufficient water, usually about 40 liters, reduced temperature, about 4° C. being preferred. If turbidity is apparent, the solution may be clarified by centrifugation at a reduced temperature, about 2°-6° C., and at a flow rate of about 6-7 liters per hour.

(B) Second Fractional Alcohol Precipitation

This is performed as in the first fractional alcohol precipitation by adjusting the above formed polysaccharide bearing supernatant to a pH of about 6.6 and in the preferred embodiment ±0.1 being accomplished with 8 M acetic acid. Sodium acetate is added to a final concentration of about 4% and the pH adjusted to about 6.7 and ±0.1 as above being preferred. Alcohol from about 0.5 to 1.0 volumes is added, and in the preferred embodiment 0.75 volumes, the pH adjusted to 7, and treated as described in the first fractional alcohol precipitation with stirring chilled, pH adjustment, standing and clarification through centrifugation. The precipitation thus removed, the partially purified polysaccharide supernatant fluid is adjusted to a pH of about 6.6 and in the preferred embodiment ±0.1. To fully precipitate the polysaccharide sodium acetate is added to about a 4% final concentration and the pH adjusted to about 6.7 as described in the first fractional alcohol precipitation and ±0.1 in the preferred embodiment. Alcohol from about 1.25 to 1.75 volume is added to a final minimum concentration of 1.5 volumes in the preferred embodiment and the pH adjusted to 7. This is followed by standing, as in the first fractional alcohol precipitation centrifugation and again being redissolved in about 40 liters of cold pyrogen-free water, about 4° C. in the preferred embodiment.

(C) Activated Charcoal Purification

The polysaccharide solution, still chilled, is then adjusted to a pH of about 6.1 with 0.3 M acetic acid and sodium chloride to a 0.15 M concentration. A 20% suspension of activated charcoal is added with stirring to result in a 2 to 6% concentration of activated charcoal with 4% being preferred. The mixture is permitted to stand chilled, about 4° C., for about 30 minutes. This mixture is filtered to remove activated charcoal and further clarified by passage through a series of millipore type membranes. In the preferred embodiment a 293 mm millipore housing containing a CPX-10C (AMF-CUNO pad) apparatus was used and 1.2, 0.65, 0.45, and 0.22u millipore membranes. During this procedure optical density at 260 MU is monitored as a check on nucleic acid concentration and the method of Lowry et al. is used to monitor protein content.

The resultant filtrate is warmed to room temperature around 21°-25° C., prior to diafiltration. Here a model DC30 Amicon unit was used containing a hollow fiber cartridge with a 10,000 M.W. cut off, and all residual sodium chloride removed. The diafiltrate is then quick frozen, and lyophilized leaving purified pneumococcal polysaccharide powder, herein of Type 18C. This powder is harvested under low humidity into jars which are then tightly sealed and stored super cold, below −20° C. being found suitable.

The above process has removed more than 99% of contaminant protein and nucleic acid while retaining the immunogenicity of the product.

We claim:

1. A process for purification of effectively immunogenic Type 1 pneumococcal capsular polysaccharide from a clarified fermentation lysate by a process comprising
   (a) fractionally precipitating from 0.25 to 0.5 volumes of alcohol, the lysate being a a pH of about 6.7 and having a final sodium acetate concentration of about 4% and being at a temperature of 2°-6° C., and removing contaminants so precipitated and,
   (b) precipitating Type 1 polysaccharide with from about 0.5 to about 1.0 volume of alcohol at a pH of about 6.7, and
   (c) collecting and redissolving such precipitate, and
   (d) repeating step a at about 0.15 to 0.35 volumes of alcohol, and
   (e) repeating step b and at 0.5 to 1.0 volumes of alcohol and then repeating step c, and
   (f) fractionally precipitating the redissolved precipitate of (e) with cetavlon at a temperature of from 21°-25° C. and a pH of 7.4±0.1, and a cetavlon concentration of 1.5 to 5.0 volumes percent, and based on a 10% cetavlon solution, and
   (g) removing the precipitated polysaccharide and redissolving the polysaccharide in about 0.25 M NaCl while chilled, and
   (h) reprecipitating the polysaccharide at a pH of about 6.7 with about 4% sodium acetate and about 1 volume of alcohol, and redissolving in pyrogen-free water, and
   (i) repeating step (h) 2 times, and
   (j) purifying the polysaccharide solution of (i) with activated charcoal at a pH of 6.1 and a sodium chloride concentration of 0.15 M by adding activated charcoal in suspension to concentration of from 3% to 7% based on a 20% activated charcoal suspension and the solution standing chilled for about 30 minutes and filtering out said activated charcoal, and
   (k) diafiltering the solution against distilled water, and
   (l) freezing and lyophilizing the resultant product.

2. The process of claim 1 wherein Step a utilizes 0.4 volumes of alcohol for fractional precipitations.

3. The process of claim 1 wherein Step d utilizes 0.25 volumes of alcohol for fractional precipitation.

4. The process of claim 1 wherein Step f utilizes 2.5 volumes percent cetavlon for precipitation.

5. The process of claim 1 wherein Step j utilizes 5 volumes percent activated charcoal.

6. A process for purification of effectively immunogenic Type 2 pneumococcal capsular polysaccharide from a clarified fermentation lysate by a process comprising
   (a) fractionally precipitating with 0.25 to 0.75 volumes of alcohol, the lysate being at a pH of about 6.7 and having a final sodium acetate concentration of about 4% and being at a temperature of 2°-6° C., and removing contaminants so precipitated and,
   (b) precipitating Type 2 polysaccharide with from about 1.0 to about 1.5 volume of alcohol at a pH of about 6.7, and
   (c) collecting and redissolving such precipitate, and
   (d) repeating Step a at about 0.25 to 0.75 volumes of alcohol, and
   (e) repeating step c and at 1.0 to 1.5 volumes of alcohol and then repeating stpe c and
   (f) fractionally precipitating the redissolved precipitate of (e) with cetavlon at a temperature of from 21°-25° C. and a pH of 7.4±0.1 and cetavlon concentration of 1.0 to 3.0 volumes percent based on a 10% cetavlon solution, and
   (g) removing the precipitated polysaccharide and redissolving the polysaccharide in about 0.25 M NaCl while chilled, and
   (h) reprecipitating the polysaccharide at a pH of about 6.7 with about 4% sodium acetate and about 0.25 volume of alcohol, and redissolving in pyrogen-free water, and
   (i) repeating Step (h) 2 times, and
   (j) purifying the polysaccharide solution of (i) with activated charcoal at a pH of 6.1 and a sodium chloride concentration of 0.15 M, by adding activated charcoal in suspension to concentration of from 3% to 7% based on a 20% activated charcoal suspension and the solution standing chilled for about 30 minutes and filtering out said activated charcoal, and
   (k) diafiltering the solution against distilled water, and 7. The process of claim 10 wherein Step a utilizes 0.5 volumes of alcohol for fractional precipitations.

8. The process of claim 6 wherein Step d utilizes 0.5 volumes of alcohol for fractional precipitation.

9. The process of claim 6 wherein Step f utilizes 2.0 volumes percent cetavlon for precipitation.

10. The process of claim 6 wherein Step j utilizes 5 volumes percent activated charcoal.

11. A process for purification of effectively immunogenic Type 4 pneumococcal capsular polysaccharide essentially free of "C" polysaccharide from a clarified fermentation lysate by a process comprising
   (a) fractionally precipitating with 0.5 to 1.0 volumes of alcohol, the lysate being at a pH of about 6.7 and having a final sodium acetate concentration of about 4% and being at a temperature of 2°-6° C., and removing contaminants so precipitated and,
   (b) precipitating Type 4 polysaccharide with from about 2.25 to about 2.75 volume of alcohol at a pH of about 6.7, and
   (c) collecting and redissolving such precipitate, and,
   (d) repeating Step a at about 0.75 to 1.25 volumes of alcohol, and
   (e) repeating Step b and at 2.25 to 3.0 volumes of alcohol and then repeating Step c and
   (f) fractionally precipitating the redissolved precipitate of (e) with cetavlon at a temperature of from 21°-25° C. and a pH of 7.4±0.1 and cetavlon concentration of 1.5 to 5.0 volumes percent based on a 10% cetavlon solution, and (g) removing the precipitated polysaccharide and redissolving the polysaccharide in about 1.0 NaCl while chilled, and (h) reprecipitating the polysaccharide at a pH of about 6.7 with about 4% sodium acetate and about 2.75 volume of alcohol, and redissolving in pyrogen-free water, and (i) repeating Step h 2 times, and (j) adding to the solution of Step (i) at 4° C. and a pH of about 3 ammonium sulphate to a concentration of 25 to 45% for preferentially permitting type 4 polysaccharide to precipitate while "C" polysaccharide remains in solution centrifuging and resuspending the type 4 polysaccharide essentially free of "C" polysaccharide in water, and (k) purifying the polysaccharide solution of (i) with activated charcoal at a pH of 6.1 and a sodium chloride concentration of 0.15 M, by adding activated charcoal in suspension to concentration of from 1% to 3% based on a 20% activated charcoal suspension and the solution standing chilled for about 30 minutes and filtering out said activated charcoal, and (l) diafiltering the solution against distilled water, and (m) freezing and lyophilizing the resultant product.

12. The process of claim 11 wherein Step a utilizes 0.75 volumes of alcohol for fractional precipitation.

13. The process of claim 11 wherein Step d utilizes 1.0 volumes of alcohol for fractional precipitation.

14. The process of claim 11 wherein Step f utilizes 2.0 volumes percent cetavlon for precipitation.

15. The process claim wherein Step j utilizes 35% ammonium sulfate.

16. The process of claim 15 wherein Step k utilizes 2 volumes percent activated charcoal.

17. A process for purification of effectively immunogenic Type 8 pneumococcal capsular polysaccharide from a clarified fermentation lysate by a process comprising (a) precipitating with 0.25 to 0.75 volumes of alcohol, the lysate being at a pH of about 6.7 and having a final sodium acetate concentration of about 4% and being at a temperature of 2°-6° C., and removing contaminants not precipitated and, (b) collecting and redissolving such precipitate, and (c) repeating Step a at about 0.5 to 1.0 volumes of alcohol, and (d) repeating Step b and (e) fractionally precipitating the dissolved polysaccharide fraction of (c) with cetavlon at a temperature of from 21°-25° C. and a pH of 7.4±0.1, and a cetavlon concentration of 3.0 to 5.0 volumes percent based on a 10% cetavlon solution, and (f) removing the precipitated polysaccharide and redissolving the polysaccharide in about 0.25 M NaCl while chilled, and (g) reprecipitating the polysaccharide at a pH of about 6.7 with about 4% sodium acetate and about 0.75 volume of alcohol, and redissolving in pyrogen-free water, and (h) repeating step (h) 2 times, and (i) purifying the polysaccharide solution of (i) with activated charcoal at a pH of 6.1 and a sodium chloride concentration of 0.15 M, by adding activated charcoal in suspension to concentration of from 2% to 6% based on a 20% activated charcoal suspension, and the solution standing chilled for about 30 minutes and filtering out said activated charcoal, and (j) diafiltering the solution against distilled water, and (k) freezing and lyophilizing the resultant product.

18. The process of claim 17 wherein Step a utilizes 0.5 volumes of alcohol for precipitations.

19. The process of claim 17 wherein Step c utilizes 0.75 volumes of alcohol for precipitation.

20. The process of claim 17 wherein Step e utilizes 4.0 volumes percent cetavlon for precipitation.

21. The process of claim 17 wherein Step j utilizes 4 volumes percent activated charcoal.

22. A process for purification of effectively immunogenic Type 12F pneumococcal capsular polysaccharide from a clarified fermentation lysate by a process comprising (a) fractionally precipitating with 0.25 to 0.55 volumes of alcohol, the lysate being at a pH of about 6.7 and having a final sodium acetate concentration of about 4% and being at a temperature of 2°-6° C., and removing contaminants so precipitated and, (b) precipitating Type 12F polysaccharide with from about 0.75 to about 1.25 volume of alcohol at a pH of about 6.7, and (c) collecting and redissolving such precipitate, and (d) repeating Step a at about 0.25 to 0.55 volumes of alcohol, and (e) repeating Step b at 0.75 to 1.25 volumes of alcohol and then repeating Step c and, (f) fractionally precipitating the redissolved precipitate of (e) with cetavlon at a temperature of from 21°-25° C. and a pH of 7.4±0.1, and a cetavlon concentration of 1.0 to 3.5 volumes percent, based on a 10% cetavlon solution, and (g) removing the precipitated polysaccharide and redissolving the polysaccharide in about 0.25 M NaCl while chilled, and (h) reprecipitating the polysaccharide at a pH of about 6.7 with about 4% sodium acetate and about 1.25 volumes of alcohol, and redissolving in pyrogen-free water, and (i) repeating Step h 2 times, and (j) purifying the polysaccharide solution of (i) with activated charcoal at a pH of 6.1 and a sodium chloride concentration of 0.14 M by adding activated charcoal in suspension to concentration of from 1.0 to 5.0% based on a 20% activated charcoal suspension and the solution standing chilled for about 30 minutes and filtering out said activated charcoal, and (k) diafiltering the solution against distilled water, and (l) freezing and lyophilizing the resultant product.

23. The process of claim 22 wherein Step a utilizes 0.4 volumes of alcohol for fractional precipitations.

24. The process of claim 22 wherein Step d utilizes 0.4 volumes of alcohol for fractional precipitation.

25. The process of claim 22 wherein Step f utilizes 2.0 volumes percent cetavlon for precipitation.

26. The process of claim 22 wherein Step j utilizes 3 volumes percent activated charcoal.

27. A process for purification of effectively immunogenic Type 25 pneumococcal capsular polysaccharide from a clarified fermentation lysate by a process comprising (a) fractionally precipitating with 0.25 to 0.75 volumes of alcohol, the lysate being at a pH of about 6.7 and having a final sodium acetate concentration of about 4% and being at a temperature of 2°-6° C., and removing contaminants so precipitated and,
(b) precipitating Type 25 polysaccharide with from about 1.25 to about 1.75 volume of alcohol at a pH of about 6.7, and
(c) collecting and redissolving such precipitate, and
(d) repeating Step a at about 0.25 to 0.75 volumes of alcohol, and
(e) repeating Step b at about 1.5 to 2.0 volumes of alcohol and repeating Step c and
(f) fractionally precipitating the redissolved precipitate of (e) with cetavlon at a temperature of from 21°-25° C. and a pH of 7.4±0.1, and a cetavlon concentration of 4.0 to 8.0 volumes percent based on a 10% cetavlon solution, and
(g) removing the precipitated polysaccharide and redissolving the polysaccharide in about 0.25 M NaCl while chilled, and
(h) reprecipitating the polysaccharide at a pH of about 6.7 with about 4% sodium a etate and about 1.75 volumes of alcohol, and redissolving in pyrogen-free water, and
(i) repeating Step h 2 times, and
(j) purifying the polysaccharide solution of (i) with activated charcoal at a pH of 6.1 and a sodium chloride concentration of 0.15 M by adding activated charcoal in suspension to concentration of from 5% to 9% based on a 20% activated charcoal suspension and the solution standing chilled for about 30 minutes and filtering out said activated charcoal, and
(k) diafiltering the solution against distilled water, and
(l) freezing and lyophilizing the resultant product.

28. The process of claim 27 wherein Step a utilizes 0.5 volumes of alcohol for fractional precipitations.

29. The process of claim 27 wherein Step d utilizes 0.5 volumes of alcohol for fractional precipitation.

30. The process of claim 27 wherein Step f utilizes 6.0 volumes percent cetavlon for precipitation.

31. The process of claim 27 wherein Step j utilizes 7 volumes percent activated charcoal.

32. A process for purification of effectively immunogenic Type 6A pneumococcal capsular polysaccharide from a clarified fermentation lysate by a process comprising
(a) fractionally precipitating with 0.4 to 0.6 volumes of alcohol, the lysate being at a pH of about 6.7 and having a final sodium acetate concentration of about 4% and being at a temperature of 2°-6° C., and removing contaminants so precipitated and,
(b) precipitating Type 6A polysaccharide with from about 1.25 to about 1.75 volume of alcohol at a pH of about 6.7, and
(c) collecting and redissolving such precipitate, and
(d) repeating Step a at about 0.4 to 0.6 volumes of alcohol, and
(e) repeating Step b and repeating Step c
(f) repeating Step a with 0.5 to 1.0 volumes of alcohol and,
(g) repeating Step e, and
(h) fractionally precipitating impurities from the polysaccharide of (g) with cetavlon at a temperature of from 21°-25° C. and 0.15 M NaCl and a pH of 7.0±0.1, and a cetavlon concentration of 0.05 to 0.2 volumes percent based on a 10% cetavlon solution, and
(i) reprecipitating the polysaccharide at a pH of about 6.7 with about 4% sodium acetate and about 1.5 volume of alcohol, and redissolving in pyrogen-free water, and
(j) repeating Step i 2 times, and
(k) purifying the polysaccharide solution of (j) with activated charcoal at a pH of 6.1 and a sodium chloride concentration of 0.15 M, by adding activated charcoal in suspension to concentration of from 5% to 9% based on a 20% activated charcoal suspension, and the solution standing chilled for about 30 minutes and filtering out said activated charcoal, and
(l) diafiltering the solution against distilled water, and
(m) freezing the lyophilizing the resultant product.

33. The process of claim 32 wherein Step a utilizes 0.5 volumes of alcohol for fractional precipitation.

34. The process of claim 32 wherein Step d utilizes 0.5 volumes of alcohol for fractional precipitation.

35. The process of claim 32 wherein Step f utilizes 0.75 volumes of alcohol for fractional precipitation.

36. The process of claim 32 wherein Step h utilizes 0.1 volumes percent cetavlon for precipitation.

37. The process of claim 32 wherein Step k utilizes 7 volumes percent activated charcoal.

38. A process for purification of effectively immunogenic Type 6B pneumococcal capsular polysaccharide from a clarified fermentation lysate by a process comprising
(a) fractionally precipitating with 0.4 to 1.6 volumes of alcohol, the lysate being at a pH of about 6.7 and having a final sodium acetate concentration of about 4% and being at a temperature of 2°-6° C., and removing contaminants so precipitated and,
(b) precipitating Type 6B polysaccharide with from about 1.25 to about 1.75 volumes of alcohol at a pH of about 6.7, and
(c) collecting and redissolving such precipitate, and
(d) repeating Step a at about 0.15 to 0.35 volumes of alcohol, and
(e) repeating Step b and repeating Step c
(f) repeating Step a with 0.25 to 0.75 volumes of alcohol and,
(g) repeating Step e, and
(h) fractionally precipitating impurities from the polysaccharide of (g) with cetavlon at a temperature of from 21°-25° C. and 0.15 M NaCl and a pH of 7.4±0.1, and a cetavlon concentration of 0.3 to 0.5 volumes percent based on a 10% cetavlon solution, and
(i) reprecipitating the polysaccharide at a pH of about 6.7 with about 4% sodium acetate and about 1.5 volumes of alcohol, and redissolving in pyrogen-free water, and
(j) repeating Step i 2 times, and
(k) purifying the polysaccharide solution of (j) with activated charcoal at a pH of 6.1 and a sodium chloride concentration of 0.15 M by adding activated charcoal in suspension to concentration of from 6% to 10% based on a 20% activated charcoal suspension and the solution standing chilled for about 30 minutes and filtering out said activated charcoal, and
(l) diafiltering the solution against distilled water, and
(m) freezing and lyophilizing the resultant product.

39. The process of claim 38 wherein Step a utilizes 0.5 volumes of alcohol for fractional precipitation.

40. The process of claim 38 wherein Step d utilizes 0.25 volumes of alcohol for fractional precipitation.

41. The process of claim 38 wherein Step f utilizes 0.5 volumes of alcohol for fractional precipitation.

42. The process of claim 38 wherein Step h utilizes 0.4 volumes percent cetavlon for precipitation.

43. The process of claim 38 wherein Step k utilizes 8 volumes percent activated charcoal.

44. A process for purification of effectively immunogenic Type 7F pneumococcal capsular polysaccharide essentially free of "C" polysaccharide from a clarified fermentation lysate by a process comprising
   (a) fractionally precipitating with 0.75 to 1.25 volumes of alcohol, the lysate being at a pH of about 6.7 and having a final sodium acetate concentration of about 4% and being at a temperature of 2°-6° C., and removing contaminants so precipitated and,
   (b) precipitating Type 7F polysaccharide with from about 2.5 to about 3.0 volumes of alcohol at a pH of about 6.7, and
   (c) collecting and redissolving such precipitate, and
   (d) repeating Step a at about 0.75 to 1.25 volumes of alcohol, and
   (e) repeating Step b precipitating with from 2.25 to 2.75 volumes of alcohol and repeating Step c,
   (f) fractionally precipitating impurities from the polysaccharide of (e) with cetavlon at a temperature of from 21°-25° C. and 0.15 M NaCl and a pH of 7.4±0.1, and a cetavlon concentration of 0.02 to 1.5 volumes percent, based on a 10% cetavlon solution, and
   (g) reprecipitating the polysaccharide at a pH of about 6.7 with about 4% sodium acetate and about 2.75 volumes of alcohol, and redissolving in pyrogen-free water, and
   (h) repeating Step g 2 times, and
   (i) adding to the solution of Step h at 4° C. and at a pH of about 7 ammoniu sulfate to a concentration of 35 to 60% preferentially permitting type 7F polysaccharide to precipitate while "C" polysaccharide remains in solution, centrifuging, and resuspending the Type 7F polysaccharide essentially free of "C" polysaccharide in water, and
   (j) purifying the polysaccharide solution of (h) with activated charcoal at a pH of 6.1 and adding activated charcoal in suspension to concentration of from 1% to 3% based on a 20% activated charcoal suspension, and the solution standing chilled for about 30 minutes and filtering out said activated charcoal, and
   (k) diafiltering the solution against distilled water, and
   (l) freezing and lyohpilizing the resultant product.

45. The process of claim 44 wherein Step a utilizes 1.0 volumes of alcohol for fractional precipitation.

46. The process of claim 44 wherein Step d utilizes 1.0 volumes of alcohol for fractional precipitation.

47. The process of claim 44 wherein Step f utilizes 0.075 volumes percent cetavlon for precipitation.

48. The process of claim 44 wherein Step i utilizes a concentration of 50% ammonium sulfate.

49. The process of claim 44 wherein Step j utilizes 2 volumes percent activated charcoal.

50. A process for purification of effectively immunogenic Type 9N pneumococcal capsular polysaccharide from a clarified fermentation lysate by a process comprising
   (a) fractionally precipitating with 0.5 to 1.0 volumes of alcohol, the lysate being at a pH of about 6.7 and having a final sodium acetate concentration of about 4% and being at a temperature of 2°-6° C., and removing contaminants so precipitated and,
   (b) precipitating Type 9N polysaccharide with from about 1.0 to about 1.5 volume of alcohol at a pH of about 6.7, and
   (c) collecting and redissolving such precipitate, and
   (d) repeating Step a at about 0.15 to 0.75 volumes of alcohol, and
   (e) repeating Step b and repeating Step C
   (f) fractionally precipitating impurities from the polysaccharide of (e) with cetavlon at a temperature of from 21°-25° C. and a pH of 7.4±0.1, and a cetavlon concentration of 0.05 to 0.5 volumes percent based on a 10% cetavlon solution, and
   (g) reprecipitating the polysaccharide at a pH of about 6.7 with about 4% sodium acetate and about 1.25 volumes of alcohol, and redissolving in pyrogen-free water, and
   (h) repeating Step g 2 times, and
   (i) purifying the polysaccharide solution of (h) with activated charcoal at a pH of 6.1 and adding activated charcoal in suspension to concentration of from 2% to 6%, and the solution standing chilled for about 30 minutes and filtering out said activated charcoal, and
   (j) diafiltering the solution against distilled water, and
   (k) freezing and lyophilizing the resultant product.

51. The process of claim 50 wherein Step a utilizes 0.75 volumes of alcohol for fractional precipitation.

52. The process of claim 50 wherein Step d utilizes 0.5 volumes of alcohol for fractional precipitation.

53. The process of claim 50 wherein Step f utilizes 0.1 volumes percent cetavlon for precipitation.

54. The process of claim 50 wherein Step k utilizes volumes percent activated charcoal.

55. A process for purification of effectively immunogenic Type 14 pneumococcal capsular polysaccharide essentially free of "C" polysaccharide from a clarified fermentation lysate by a process comprising
   (a) fractionally precipitating with 0.1 to 0.5 volumes of alcohol, the lysate being at a pH of about 6.7 and having a final sodium acetate concentration of about 4% and being at a temperature of 2°-6° C., and removing contaminants so precipitated and,
   (b) precipitating Type 14 polysaccharide with from about 1.25 to about 1.75 volume of alcohol at a pH of about 6.7, and
   (c) collecting and redissolving such precipitate,
   (d) repeating Step a at about 0.2 to 0.6 volumes of alcohol, and
   (e) repeating Step b and repeating Step c
   (f) fractionally precipitating impurities from the polysaccharide of (e) with cetavlon at a temperature of from 21°-25° C. and a pH of 7.4±0.1, and a cetavlon concentration of 0.05 to 0.3 volumes percent based on a 10% cetavlon solution, and
   (g) reprecipitating the polysaccharide at a pH of about 6.7 with about 4% sodium acetate and about 1.5 volumes of absolute methanes, and redissolving in pyrogen-free water, and
   (h) repeating Step g 2 times, using 1.5 volumes of alcohol and,
   (i) purifying the polysaccharide solution of (h) with activated charcoal at a pH of 6.1 and a sodium chloride concentration of 0.1 M, by adding activated charcoal in spension to concentration of from 2% to 6% based on a 20% activated charcoal suspension and the solution standing chilled for about 30 minutes and filtering out said activated charcoal, and (l) diafiltering the solution against a distilled water, and (m) freezing and lyophilizing the resultant product.

56. The process of claim 55 wherein Step a utilizes 0.25 volumes of alcohol for fractional precipitation.

57. The process of claim 55 wherein Step d utilizes 0.4 volumes of alcohol for fractional precipitation.

58. The process of claim 55 wherein Step f utilizes 0.1 volumes percent cetavlon for precipitation.

59. The process of claim 55 wherein Step i utilizes 4 volumes percent activated charcoal.

60. A process for purification of effectively immunogenic Type 19F pneumococcal capsular polysaccharide from a clarified fermentation lysate by a process comprising (a) fractionally precipitating with 0.25 to 0.75 volumes of alcohol, the lysate being at a pH of about 6.7 and having a final sodium acetate concentration of about 4% and being at a temperature of 2°–6° C., and removing contaminants so precipitated and, (b) precipitating Type 19F polysaccharide with from about 1.25 to about 1.75 volume of alcohol at a pH of about 6.7, and (c) collecting and redissolving such precipitate, and (d) repeating Step a at about 0.25 to 0.75 volumes of alcohol, and (e) repeating Step b and repeating Step c (f) fractionally precipitating impurities from the polysaccharide of (e) with cetavlon at a temperature of from 21°–25° C. and 0.15 M NaCl and a pH of 7.4±0.1, and a cetavlon concentration of 0.05 to 0.4 volumes percent based on a 10% cetavlon solution and (g) reprecipitating the polysaccharide at a pH of about 6.7 with about 4% sodium acetate and about 1.5 volumes of alcohol, and redissolving in pyrogen-free water, and (h) repeating Step g 2 times, and (i) purifying the polysaccharide solution of (h) with activated charcoal at a pH of 6.1 and a sodium chloride concentration of 0.15 M, by adding activated charcoal in suspension to concentration of from 3% to 7% based on a 20% activated charcoal suspension and the solution standing chilled for about 30 minutes and filtering out said activated charcoal, and (j) diafiltering the solution against distilled water, adding 0.01 to 25 volumes percent of glycine, and (k) freezing and lyophilizing the resultant product.

61. The process of claim 60 wherein Step a utilizes 0.5 volumes of alcohol for fractional precipitation.

62. The process of claim 60 wherein Step d utilizes 0.5 volumes of alcohol for fractional precipitation.

63. The process of claim 60 wherein Step f utilizes 0.2 volumes percent cetavlon for precipitation.

64. The process of claim 60 wherein Step i utilizes 5 volumes percent activated charcoal.

65. The process of claim 60 wherein Step k utilizes 0.2 volumes percent glycine.

66. A process for purification of effectively immunogenic Type 20 pneumococcal capsular polysaccharide from a clarified fermentation lysate by a process comprising (a) fractionally precipitating with 0.25 to 0.75 volumes of alcohol, the lysate being at a pH of about 6.7 and having a final sodium acetate concentration of about 4% and being at a temperature of 2°–6° C., and removing contaminants so precipitated, and (b) precipitating Type 20 polysaccharide with from about 1.25 to about 1.75 volume of alcohol at a pH of about 6.7, and (c) collecting and redissolving such precipitate, and (d) repeating Step a at baout 0.25 to 0.75 volumes of alcohol, and (e) repeating Step b and repeating Step c (f) repeating Step a with 0.5 to 1.0 volumes of alcohol and, (g) repeating Step e (h) fractionally precipitating impurities from the polysaccharide of (g) with cetavlon at a temperature of from 21°–25° C. and 0.15 M NaCl and a pH of 7.4±0.1, and a cetavlon concentration of 0.1 to 0.5 volumes percent based on a 10% cetavlon solution, and (i) reprecipitating the polysaccharide at a pH of about 6.7 with about 4% sodium acetate and about 1.5 volumes of alcohol, and redissolving in pyrogen-free water, and (j) repeating Step i 2 times, and (k) purifying the polysaccharide solution of (j) with activated charcoal at a pH of 6.1 and a sodium chloride concentration of 0.15 M, by adding activated charcoal in suspension to concentration of from 3% to 7% based on a 20% activated charcoal suspension and the solution standing chilled for about 30 minutes and filtering out said activated charcoal, and (l) diafiltering the solution against distilled water, and (m) freezing and lyophilizing the resultant product.

67. The process of claim 66 wherein Step a utilizes 0.5 volumes of alcohol for fractional precipitation.

68. The process of claim 66 wherein Step d utilizes 0.5 volumes of alcohol for fractional precipitation.

69. The process of claim 66 wherein Step f utilizes 0.75 volumes of alcohol for fractional precipitation.

70. The process of claim 66 wherein Step h utilizes 0.25 volumes percent cetavlon for precipitation.

71. The process of claim 66, wherein Step k utilizes 5 volumes percent activated charcoal.

72. A process for purification of effectively immunogenic Type 23F pneumococcal capsular polysaccharide from a clarified fermentation lysate by a process comprising (a) fractionally precipitating with 0.25 to 0.75 volumes of alcohol, the lysate being at a pH of about 6.7 and having a final sodium acetate concentration of about 4% and being at a temperature of 2°–6° C., and removing contaminants so precipitated and, (b) precipitating Type 23F polysaccharide with from about 1.0 to about 1.5 volume of alcohol at a pH of about 6.7, and (c) collecting and redissolving such precipitate, and (d) repeating Step a at about 0.25 to 0.75 volumes of alcohol, and (e) repeating Step b and repeating Step c (f) fractionally precipitating impurities from the polysaccharide of (e) with cetavlon at a temperature of from 21–°25° C. and 0.15 M NaCl and a pH of 7.4±0.1, and a cetavlon concentration of 0.1 to 0.3 volumes percent, and (g) reprecipitating the polysaccharide at a pH of about 6.7 with about 4% sodium acetate and about 1.5 volumes of alcohol, and redissolving in pyrogen-free water, (h) repeating Step g 2 times, and (i) purifying the polysaccharide solution of (h) with activated charcoal at a pH of 6.1 and a sodium chloride concentration of 0.15 M, by adding activated charcoal in suspension to concentration of from 2% to 6% based on a 20% activated charcoal suspension and the solution standing chilled for about 30 minutes and filtering out said activated charcoal, and (j) diafiltering the solution against distilled water, and (k) freezing and lyophilizing the resultant product.

73. The process of claim 72 wherein Step a utilizes 0.5 volumes of alcohol for fractional precipitation.

74. The process of claim 72 wherein Step d utilizes 0.5 volumes of alcohol for fractional precipitation.

75. The process of claim 72 wherein Step f utilizes 0.2 volumes percent cetavlon for precipitation.

76. The process of claim 72 wherein Step i utilizes 4 volumes percent activated charcoal.

77. A process for purification of Effectively immunogenic Type 3 pneumococcal capsular polysaccharide from a clarified fermentation lysate by a Process comprising (a) precipitating with 0.15 to 0.5 volumes of alcohol, the lysate being at a pH of about 6.7 and having a final sodium acetate concentration of about 4% and being at a temperature of 2°-6° C., and (b) redissolving such precipitate, and (c) repeating Step a at about 0.25 to 0.6 volumes of alcohol, and (d) repeating Step b and, (e) repeating Step a with 0.1 to 0.5 volumes of alcohol and, (f) repeating Step b, and (g) purifying the polysaccharide solution of f with activated charcoal at a pH of 6.1 and a sodium chloride concentration of 0.15 M, by adding activated charcoal in supsension to concentration of from 0.1% to 5% based on a 20% activated charcoal suspension and the solution standing chilled for about 30 minutes and filtering out said activated charcoal, and (h) diafiltering the solution against distilled water, and (i) freezing and lyophilizing the resultant product.

78. The process of claim 77 wherein Step a utilizes 0.25 volumes of alcohol for precipitation.

79. The process of claim 77 wherein Step c utilizes 0.4 volumes of alcohol for precipitation.

80. The process of claim 77 wherein Step e utilizes 0.25 volumes of alcohol for precipitation.

81. The process of claim 77 wherein Step g utilizes 3 volumes percent activated charcoal.

82. A process for purification of Effectively immunogenic Type 18C pneumococcal capsular polysaccharide from a clarified fermentation lysate by a process comprising (a) fractionally precipitating with 0.25 to 0.75 volumes of alcohol, the lysate being at a pH of about 6.7 and having a final sodium acetate concentration of about 4% and being at a temperature of 2°-6° C., and removing contaminants so precipitated and, (b) precipitating Type 18C polysaccharide with from about 1.25 to about 1.75 volume of alcohol at a pH of about 6.7, and (c) collecting and redissolving such precipitate, and (d) repeating Step a at about 0.5 to 1.0 volumes of alcohol, and (e) repeating Step b and repeating Step c (f) purifying the polysaccharide solution of (e) with activated charcoal at a pH of 6.1 and a sodium chloride concentration of 0.15 M, by adding activated charcoal in suspension to concentration of from 2% to 6% based on a 20% activated charcoal suspension, and the solution standing chilled for about 30 minutes and filtering out said activated charcoal, and (g) diafiltering the solution against distilled water, and (h) freezing and lyophilizing the resultant product.

83. The process of claim 82 wherein Step a utilizes 0.5 volumes of alcohol for fractional precipitation.

84. The process of claim 82 wherein Step d utilizes 0.75 volumes of alcohol for fractional precipitation.

85. The process of claim 82 wherein Step f utilizes 4 volumes percent activated charcoal.

* * * * *

UNITED STATES PATENT OFFICE
CERTIFICATE OF CORRECTION

Patent No. 4,242,501          Dated December 30, 1980

Inventor(s) Francis J. Cano, Joseph S.C. Kuo, Merle Vernon Querry

It is certified that error appears in the above-identified patent and that said Letters Patent are hereby corrected as shown below:

Column 16, line 7 (Example 5, first line after the title): "6A" should read -- 12F -- .

Signed and Sealed this

Twenty-third Day of February 1982

[SEAL]

Attest:

Attesting Officer

GERALD J. MOSSINGHOFF

Commissioner of Patents and Trademarks